(12) United States Patent
Vendeville et al.

(10) Patent No.: US 7,763,641 B2
(45) Date of Patent: Jul. 27, 2010

(54) BROADSPECTRUM HETEROCYCLIC SUBSTITUTED PHENYL CONTAINING SULFONAMIDE HIV PROTEASE INHIBITORS

(75) Inventors: Sandrine Marie Helene Vendeville, Brussels (BE); Wim Gaston Verschueren, Berchem (BE); Abdellah Tahri, Anderlecht (BE); Samuel Leo Christiaan Moors, Pellenberg (BE); Montserrat Erra Sola, Vic (ES)

(73) Assignee: Tibotec Pharmaceuticals Ltd. (IE)

( * ) Notice: Subject to any disclaimer, the term of this patent is extended or adjusted under 35 U.S.C. 154(b) by 1415 days.

(21) Appl. No.: 10/499,221

(22) PCT Filed: Dec. 20, 2002

(86) PCT No.: PCT/EP02/14839

§ 371 (c)(1),
(2), (4) Date: Apr. 12, 2005

(87) PCT Pub. No.: WO03/053435

PCT Pub. Date: Jul. 3, 2003

(65) Prior Publication Data

US 2005/0222215 A1    Oct. 6, 2005

(30) Foreign Application Priority Data

Dec. 21, 2001    (EP) .................... 012051157

(51) Int. Cl.
*A61K 31/42* (2006.01)
*A61K 31/44* (2006.01)
*A61K 31/425* (2006.01)
*C07D 277/54* (2006.01)

(52) U.S. Cl. ............... 514/377; 514/338; 514/342; 514/370; 514/371; 546/270.7; 548/197; 548/198

(58) Field of Classification Search ............... 514/377, 514/338, 342, 370, 371; 548/197, 198; 546/270.7
See application file for complete search history.

(56) References Cited

FOREIGN PATENT DOCUMENTS

| EP | 0499299 | B1 | 8/2000 |
|---|---|---|---|
| EP | 0721331 | B1 | 12/2001 |
| JP | 9124630 | A | 5/1997 |
| WO | WO 94/05263 | A1 | 3/1994 |
| WO | WO 95/06030 | A1 | 3/1995 |
| WO | WO 96/22287 | A1 | 7/1996 |
| WO | WO 96/28418 | A1 | 9/1996 |
| WO | WO 96/28463 | A1 | 9/1996 |
| WO | WO 96/28464 | A1 | 9/1996 |
| WO | WO 96/28465 | A1 | 9/1996 |
| WO | WO 96/33184 | A1 | 10/1996 |
| WO | WO 97/18205 | A1 | 5/1997 |
| WO | WO 97/44014 | A1 | 11/1997 |
| WO | WO 98/42318 | A1 | 10/1998 |
| WO | WO 99/33792 | A2 | 7/1999 |
| WO | WO 99/33793 | A2 | 7/1999 |
| WO | WO 99/33795 | A1 | 7/1999 |
| WO | WO 99/33815 | A1 | 7/1999 |
| WO | WO 99/67254 | A2 | 12/1999 |

OTHER PUBLICATIONS

Banker (Modern Pharmaceutics)Banker, G.S. et al., "Modern Pharmaceutics, 3ed" Marcel Dekker, New York, 1996, pp. 451 and 596.*
West, Anthony R., Solid State Chemistr and its Applications, Wiley, New York, 1988, pp. 358 and 365.*
Wolff, Manfred E. Burger's Medicinal Chemistry, 5ed, Part I, John Wiley and Sons, 1995, pp. 975-977.*
Vippagunta et al., "Crystalline Solids" Advanced Drug Delivery Reviews 48(2001) 3-26.*
International Search Report, International Application No. PCT/EP02/14839, Date of Mailing of International Search Reoprt Mar. 21, 2003.
Chou T. et al., "Quantitative Analysis of Dose-Effect Relationships: The Combined Effects of Multiple Drugs or Enzyme Inhibitors." *Adv. Enzyme Regul.*, 1984, pp. 27-55, 22.
Cross, et al., "Rules For The Nomenclature of Organic Chemistry, Section E: Stereochemistry." *Pure & Applied Chemistry*, 1976, pp. 11-30, vol. 45., Pergamon Press, Great Britain.
Benet, L et al., "Pharmacokinetics: The Dynamics of Drug Absorption, Distribution, and Elimination," *Goodman and Gilman's The Pharmacological Basis of Therapeutics*, Eighth Edition, pp. 13-20, McGraw-Hill Inc, Jun. 1990.

(Continued)

Primary Examiner—Peter G O'Sullivan

(57) ABSTRACT

The present invention concerns the compounds having the formula (I), N-oxides, salt, stereoisomeric forms, racemic mixtures, prodrugs, esters and metabolites thereof, wherein Haryl is an aromatic monocyclic, bicyclic or tricyclic heterocycle having 3 to 14 ring members which contains one or more heteroatom ring members selected from nitrogen, oxygen and sulfur and which may optionally be substituted on (i) one or more carbon atoms by $C_{1-6}$alkyl, halogen, hydroxy, optionally mono- or disubstituted amino, nitro, cyano, halo$C_{1-6}$alkyl, carboxyl, $C_{3-7}$cycloalkyl, optionally mono- or disubstituted aminocarbonyl, methylthio, methylsulfonyl, aryl, —$(R_{7a})_n$—M—$R_{7b}$, $Het^1$ and $Het^2$; whereby the optional substituents on any amino function are independently selected from $R_5$ and —A—$R_6$; and on (ii) a nitrogen atom if present by hydroxy or —A—$R_6$. It further relates to their use as broadspectrum HIV protease inhibitors, processes for their preparation as well as pharmaceutical compositions and diagnostic kits comprising them. It also concerns combinations thereof with another anti-retroviral agent, and to their use in assays as reference compounds or as reagents.

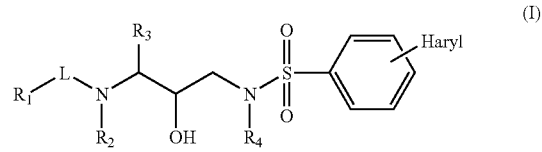

(I)

22 Claims, No Drawings

OTHER PUBLICATIONS

Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs.", *Antimicrobial Agents and Chemotherapy*, Feb. 1998, pp. 269-276, vol. 42, No. 2.

* cited by examiner

BROADSPECTRUM HETEROCYCLIC SUBSTITUTED PHENYL CONTAINING SULFONAMIDE HIV PROTEASE INHIBITORS

RELATED APPLICATIONS

This Application is a National Stage Application under 35 U.S.C. 371 of PCT/EP02/14839, filed Dec. 20, 2002, which claims priority benefit of EP 01205115.7, flied on Dec. 21, 2001.

The present invention relates to heterocyclic substituted phenyl containing sulfonamides, their use as aspartic protease inhibitors, in particular as broad spectrum HIV protease inhibitors, processes for their preparation as well as pharmaceutical compositions and diagnostic kits comprising them. The present invention also concerns combinations of the present substituted phenyl containing sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Distinct families have been identified, such as HIV-1 and HIV-2. Hereinafter, HIV will be used to generically denote these viruses.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), nucleotide reverse transcriptase inhibitors (NtRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favorable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance, have a good bioavailability and experience little or no effect on their potency due to plasma protein binding. Furthermore there is a continued need for compounds with an improved therapeutic index.

Up until now, several protease inhibitors are on the market or are being developed. One particular core structure (depicted below) has been disclosed in a number of references, such as, WO 95/06030, WO 96/22287, WO 96/28418, WO 96/28463, WO 96/28464, WO 96/28465 and WO 97/18205. The compounds disclosed therein are described as retroviral protease inhibitors.

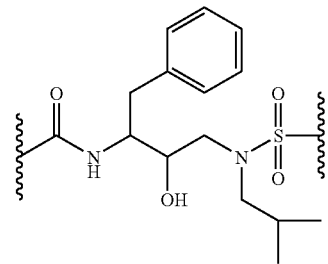

WO 99/67254 discloses 4-substituted-phenyl sulfonamides capable of inhibiting multi-drug resistant retroviral proteases.

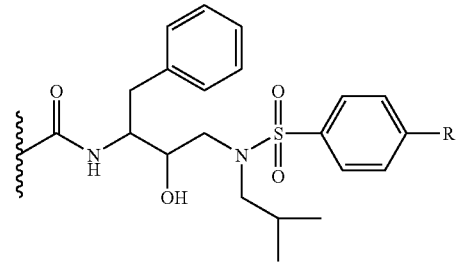

JP 9124630 and WO 96/33184 also disclose substituted phenyl sulfonamides as inhibitors of the HIV protease.

Surprisingly, the heterocyclic substituted phenyl containing sulfonamides of the present invention are found to have a favorable pharmacological and pharmacokinetic profile. Not only are they active against wild-type HIV virus, but they also show a broad spectrum activity against various mutant HIV viruses exhibiting resistance against known protease inhibitors.

The present invention concerns heterocyclic substituted phenyl containing HIV protease inhibitors, having the formula

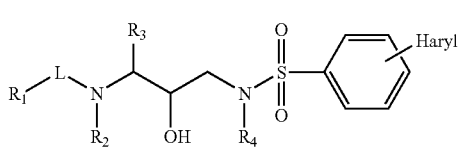

(I)

an N-oxide, salt, stereoisomeric form, racemic mixture, prodrug, ester or metabolite thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$, $Het^2$ $C_{1-6}$alkyl;

$R_1$ may also be a radical of formula

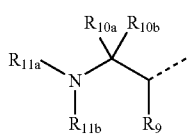

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_4$alkyl; whereby $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, $Het^1$oxycarbonyl, $Het^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkyl-carbonyloxy, arylcarbonyloxy, aryloxycarbonyloxy, $Het^1$carbonyl, $Het^1$carbonyloxy, $Het^1$ $C_{1-4}$alkyloxycarbonyl, $Het^2$carbonyloxy, $Het^2C_{1-4}$alkylcarbonyl, $Het^2C_{1-4}$alkylcarbonyloxy or $C_{1-4}$alkyl optionally substituted with aryl, aryloxy, $Het^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl $C_{1-4}$alkyl, $Het^1$, $Het^2$, $Het^1C_{1-4}$alkyl and $Het^2C_{1-4}$alkyl;

$R_{11b}$ is hydrogen, $C_{3-7}$cycloalkyl, $C_{2-6}$alkenyl, $C_{2-6}$alkynyl, aryl, $Het^1$, $Het^2$ or $C_{1-4}$alkyl optionally substituted with halogen, hydroxy, $C_{1-4}$alkylS(=O)$_t$, aryl, $C_{3-7}$cycloalkyl, $Het^1$, $Het^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

whereby $R_{11b}$ may be linked to the remainder of the molecule via a sulfonyl group;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$ whereby either the C(=O) group or the S(=O)$_2$ group is attached to the NR$_2$ moiety, $R_3$ is $C_{1-6}$alkyl, aryl, $C_{3-7}$cycloalkyl, $C_{3-7}$cycloalkyl $C_{1-4}$alkyl, or aryl$C_{1-4}$alkyl;

$R_4$ is hydrogen, $C_{1-4}$alkyloxycarbonyl, carboxyl, optionally mono- or disubstituted aminocarbonyl, $C_{3-7}$cycloalkyl, $C_{2-6}$alkenyl, $C_{2-6}$alkynyl or $C_{1-6}$alkyl, whereby $C_{3-7}$cycloalkyl, $C_{2-6}$alkenyl, $C_{2-6}$alkynyl and $C_{1-6}$alkyl may optionally be substituted with a substituent selected from aryl, $Het^1$, $Het^2$, $C_{3-7}$cycloalkyl, $C_{1-4}$alkyloxycarbonyl, carboxyl, optionally mono- or disubstituted amino-carbonyl, optionally mono- or disubstituted aminosulfonyl, $C_{1-4}$alkylS(=O)$_t$, hydroxy, cyano, optionally mono- or disubstituted amino and halogen, and whereby the optional substituents on any amino function are independently selected from $C_{1-4}$alkyl, aryl, aryl$C_{1-4}$alkyl, $C_{3-7}$cycloalkyl, $C_{3-7}$cycloalkyl-$C_{1-4}$alkyl, $Het^1$, $Het^2$, $Het^1C_{1-4}$alkyl and $Het^2C_{1-4}$alkyl; t is zero, 1 or 2;

each t independently selected is zero, 1 or 2;

Haryl is an aromatic monocyclic, bicyclic or tricyclic heterocycle having 3 to 14 ring members which contains one or more heteroatom ring members selected from nitrogen, oxygen and sulfur and which may optionally be substituted on (i) one or more carbon atoms by $C_{1-6}$alkyl, halogen, hydroxy, optionally mono- or disubstituted amino, nitro, cyano, halo$C_{1-6}$alkyl, carboxyl, $C_{3-7}$cycloalkyl, optionally mono- or disubstituted aminocarbonyl, methylthio, methylsulfonyl, aryl, —(R$_{7a}$)$_n$—M—R$_{7b}$, $Het^1$ and $Het^2$; whereby the optional substituents on any amino function are independently selected from $R_5$ and —A—$R_6$; and on (ii) a nitrogen atom if present by hydroxy or —A—$R_6$;

A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; whereby for those groups containing a $C_{1-6}$alkanediyl moiety, the $C_{1-6}$alkanediyl moiety is attached to the amino group;

$R_5$ is hydroxy, $C_{1-6}$alkyl, $Het^1C_{1-6}$alkyl, $Het^2C_{1-6}$alkyl, amino$C_{1-6}$alkyl whereby the amino group may optionally be mono- or di-substituted with $C_{1-4}$alkyl;

$R_6$ is hydrogen, $C_{1-6}$alkyloxy, $Het^1$, $Het^1$oxy, $Het^2$, $Het^2$oxy, aryl, aryloxy or amino; and in case —A— is other than $C_{1-6}$alkanediyl then $R^6$ may also be $C_{1-6}$alkyl, $Het^1C_{1-4}$alkyl, $Het^1$oxy$C_{1-4}$alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl; whereby each of the amino groups in the definition of $R_6$ may optionally be substituted with one or two substituents selected from $C_{1-4}$alkyl, $C_{1-4}$alkylcarbonyl, $C_{1-4}$allyloxycarbonyl, aryl, arylcarbonyl, aryloxycarbonyl, $Het^1$, $Het^2$, aryl$C_{1-4}$alkyl, $Het^1C_{1-4}$alkyl or $Het^2C_{1-4}$alkyl;

$R_{7a}$ is $C_{1-8}$ alkanediyl optionally substituted with one or more substituents selected from, halogen, $C_{1-4}$alkylcarbonyl, $C_{1-4}$alkyloxycarbonyl, aryl, arylcarbonyl, aryloxycarbonyl, $Het^1$ or $Het^2$;

$R_{7b}$ is $C_{1-8}$ alkyl optionally substituted with one or more substituents selected from halogen, $C_{1-4}$alkylcarbonyl, $C_{1-4}$alkyloxycarbonyl, aryl, arylcarbonyl, aryloxycarbonyl, $Het^1$ or $Het^2$;

M is defined by —C(=O), —O—C(=O)—, —C(=O)—O—, —CH$_2$—CHOH—, —CHOH—CH$_2$—, —NR$_8$—C(=O)—, —(C=O)—NR$_8$—, —S(=O)$_2$—, —O—, —S—, —O—S(=O)$_2$—, —S(=O)$_2$—O—, —NR$_8$—S(=O)$_2$ or —S(=O)$_2$—NR$_8$—;

n is zero or 1.

This invention also envisions the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides.

Whenever the term "substituted" is used in defining the compounds of formula (I), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl, 2-methyl-propyl, and the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-8}$alkyl" as a group or part of a group defines straight and branched chained saturated hydrocarbon radicals having from 1 to 8 carbon atoms, such as, those defined for $C_{1-6}$alkyl and heptyl, octyl, 2-methyl-hetyl, 3-ethyl-hexyl and the like.

The term "$C_{1-6}$alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "$C_{1-8}$alkanediyl" as a group or part of a group defines bivalent straight and branched chained saturated hydrocarbon radicals having from 1 to 8 carbon atoms such as, those defied for $C_{1-6}$alkanediyl and 2-ethyl-hexan-1,6-diyl, 3-methyl-heptan-1,7-diyl, and the like.

The term "$C_{2-6}$alkenyl" as a group or part of a group defines straight and branched chained hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include mono-, bi-, and tricyclic aromatic carbocycles such as phenyl and naphtyl which both may be optionally substituted with one or more substituents independently selected from $C_{1-6}$alkyl, $C_{1-6}$alkyloxy, halogen, hydroxy, optionally mono- or disubstituted amino, nitro, cyano, hydroxy$C_{1-6}$alkyl, halo$C_{1-6}$alkyl, carboxyl, $C_{1-6}$alkoxycarbonyl, $C_{3-7}$cycloalkyl, $Het^1$, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, $Het^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A—, $Het^1$-A—, $Het^1C_{1-6}$alkyl, $Het^1C_{1-6}$alkyl-A—, $Het^1$oxy-A—, $Het^1$oxy$C_{1-4}$alkyl-A—, phenyl-A—, phenyl-oxy-A—, phenyl-oxy$C_{1-4}$alkyl-A—, phenyl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible disubstituted with $C_{1-4}$alkyl and whereby A is as defined above. An interesting subgroup of "aryl" as a group or part of a group is meant to include mono-, bi-, and tricyclic aromatic carbocycles such as phenyl and naphtyl which both may be optionally substituted with one or more substituents independently selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, $Het^1$, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, $Het^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A—, $Het^1$-A—, $Het^1C_{1-6}$alkyl, $Het^1C_{1-6}$alkyl-A—, $Het^1$oxy-A—, $Het^1$oxy$C_{1-4}$alkyl-A—, phenyl-A—, phenyl-oxy-A—, phenyl-oxy$C_{1-4}$alkyl-A—, phenyl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible disubstituted with $C_{1-4}$alkyl and whereby A is as defined above.

The term "halo$C_{1-6}$alkyl" as a group or part of a group is defined as $C_{1-6}$alkyl substituted with one or more halogen atoms, preferably, chloro or fluoro atoms, more preferably fluoro atoms. Preferred halo$C_{1-6}$alkyl groups include for instance trifluoro-methyl and difluoromethyl.

The term "hydroxy$C_{1-6}$alkyl" as a group or part of a group is defined as $C_{1-6}$alkyl substituted with one or more hydroxy atoms.

The term "$Het^1$" as a group or part of a group is defined as a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, oxo, optionally mono- or disubstituted amino, nitro, cyano, hydroxy $C_{1-6}$alkyl, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members which contains one or more heteroatom ring members selected from nitrogen, oxygen or sulfur and whereby the optional substituents on any amino function are independently selected from $C_{1-6}$alkyl, $C_{1-6}$alkyloxy-A—, $Het^2$-A—, $Het^2C_{1-6}$alkyl, $Het^2C_{1-6}$alkyl-A—, $Het^2$oxy-A—, $Het^2$oxy$C_{1-4}$alkyl-A—, aryl-A—, aryloxy-A—, aryloxy$C_{1-4}$alkyl-A—, aryl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above. An interesting subgroup of "$Het^1$" as a group or part of a group is defined as a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, oxo, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members which contains one or more heteroatom ring members selected from nitrogen, oxygen or sulfur and whereby the optional substituents on any amino function are independently selected from $C_{1-6}$alkyl, $C_{1-6}$alkyloxy-A—, $Het^2$-A—, $Het^2C_{1-6}$alkyl, $Het^2C_{1-6}$alkyl-A—, $Het^2$oxy-A—, $Het^2$oxy$C_{1-4}$alkyl-A—, aryl-A—, aryloxy-A—, aryloxy$C_{1-4}$alkyl-A—, aryl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above.

The term "$Het^2$" as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, optionally mono- or disubstituted amino, nitro, cyano, hydroxy$C_{1-6}$alkyl, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic heterocycle having 3 to 14 ring members; whereby the optional substituents on any amino function are independently selected from $C_{1-6}$alkyl, $C_{1-4}$alkyloxy-A—, $Het^1$-A—, $Het^1C_{1-6}$alkyl, $Het^1C_{1-6}$alkyl-A—, $Het^1$oxy-A—, $Het^1$oxy$C_{1-4}$alkyl-A—, aryl-A—, aryloxy-A—, aryloxy$C_{1-4}$alkyl-A—, aryl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above. An interesting subgroup of "$Het^2$" as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic heterocycle having 3 to 14 ring members; whereby the optional substituents on any amino function are independently selected from $C_{1-6}$alkyl, $C_{1-6}$alkyloxy-A—, $Het^1$-A—, $Het^1C_{1-6}$alkyl, $Het^1C_{1-6}$alkyl-A—, $Het^1$oxy-A—, $Het^1$oxy$C_{1-4}$alkyl-A—, aryl-A—, aryloxy-A—, aryloxy$C_{1-4}$alkyl-A—, aryl$C_{1-6}$alkyl-A—, $C_{1-6}$alkyloxy-carbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above.

As used herein, the term (=O) forms a carbonyl moiety with the carbon atom to which it is attached. The term (=O) forms a sulfoxide with the sulfur atom to which it is attached. The term $(=O)_2$ forms a sulfonyl with the sulfur atom to which it is attached.

As used herein, the term (=S) forms a thiocarbonyl moiety with the carbon atom to which it is attached.

As used herein before, the term "one or more" covers the possibility of all the available C-atoms, where appropriate, to be substituted, preferably, one, two or three.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmaco-logical Basis of Therapeutics, $8^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counter-ion is pharmaceutically or physiologically acceptable. However, salts having a pharmaceutically unacceptable counter-ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, —D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms. This asymmetric center is indicated with a asterisk (*) in the figure below.

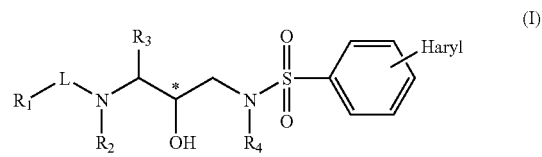

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

A particular subgroup of compounds are those compounds of formula (I), and N-oxides, salts, stereoisomeric forms, racemic mixtures, prodrugs, esters and metabolites thereof, wherein $R_1$ and $R_8$ are, each independently, hydrogen, $C_{1-4}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2$ $C_{1-6}$alkyl;

$R_1$ may also be a radical of formula

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycaxbonyl, carboxyl, aminocarbonyl, mono- or di($C_{1-4}$alkyl) aminocarbonyl, aminosulfonyl, $C_{1-4}$alkylS(O)$_r$ hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; whereby $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxy-carbonyl, Het$^2$oxycarbonyl, aryloxycarbonyl$C_{1-4}$alkyl, aryl$C_{1-4}$alkyloxy-carbonyl, $C_{1-4}$alkylcarbonyl, $C_{3-7}$cycloalkylcarbonyl, $C_{3-7}$cycloalkyl-$C_{1-4}$alkyloxycarbonyl, $C_{3-7}$cycloalkylcarbonyloxy, carboxyl$C_{1-4}$alkyl-carbonyloxy, $C_{1-4}$alkylcarbonyloxy, aryl$C_{1-4}$alkylcarbonyloxy, arylcarbonyloxy, aryloxycarbonyloxy, Het$^1$carbonyl, Het$^1$carbonyloxy, Het$^1C_{1-4}$alkyloxycarbonyl, Het$^2$carbonyloxy, Het$^2C_{1-4}$alkylcarbonyloxy, Het$^2C_{1-4}$alkyloxycarbonyloxy or $C_{1-4}$alkyl optionally substituted with aryl, aryloxy, Het$^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

whereby $R_{11b}$ may be linked to the remainder of the molecule via a sulfonyl group;

$R_2$ is hydrogen or $C_{1-6}$alkyl;

L is —C(=O)—, —O—C(=O)—, —NR$_8$—C(=O)—, —O—C$_{1-6}$alkanediyl-C(=O)—, —NR$_8$—C$_{1-6}$alkanediyl-C(=O)—, —S(=O)$_2$—, —O—S(=O)$_2$—, —NR$_8$—S(=O) whereby either the C(=O) group or the S(=O)$_2$ group is attached to the NR$_2$ moiety, $R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, optionally mono- or disubstituted aminocarbonyl, $C_{3-7}$cycloalkyl, $C_{2-6}$alkenyl, $C_{2-6}$alkynyl or $C_{1-6}$alkyl, whereby $C_{3-7}$cycloalkyl, $C_{2-6}$alkenyl, $C_{2-6}$alkynyl and $C_{1-6}$alkyl may optionally be substituted with a substituent selected from aryl, Het$^1$, Het$^2$, $C_{3-7}$cycloalkyl, $C_{1-4}$alkyloxycarbonyl, carboxyl, optionally mono- or disubstituted amino-carbonyl, optionally mono- or disubstituted aminosulfonyl, $C_{1-4}$alkylS(=O)$_t$, hydroxy, cyano, optionally mono- or disubstituted amino and halogen, and whereby the optional substituents on any amino function are independently selected from $C_{1-4}$alkyl, aryl, aryl$C_{1-4}$alkyl, $C_{3-7}$cycloalkyl, $C_{3-7}$cycloalkyl-$C_{1-4}$alkyl, Het$^1$, Het$^2$, Het$^1C_{1-4}$alkyl and Het$^2C_{1-4}$alkyl; t is zero, 1 or 2;

each t independently selected is zero, 1 or 2;

Haryl is an aromatic monocyclic, bicyclic or tricyclic heterocycle having 3 to 14 ring members which contains one or more heteroatom ring members selected from nitrogen, oxygen and sulfur and (i) which is optionally substituted on one or more carbon atoms by $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{1-6}$alkylcarbonyloxy, $C_{3-7}$cycloalkyl, optionally mono- or disubstituted aminocarbonyl, methylthio, methylsulfonyl, aryl, —(R$_{7a}$)$_n$—M—R$_{7b}$, Het$^1$ and Het$^2$; whereby the optional substituents on any amino function are independently selected from R$_5$ and —A—R$_6$; and (ii) which is optionally substituted on a nitrogen atom by hydroxy or —A—R$_6$; and A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; whereby for those groups containing a $C_{1-6}$alkanediyl moiety, the $C_{1-6}$alkanediyl moiety is attached to the amino group;

$R_5$ is hydroxy, $C_{1-6}$alkyl, Het$^1C_{1-6}$alkyl, Het$^2C_{1-6}$alkyl, amino$C_{1-6}$alkyl whereby the amino group may optionally be mono- or di-substituted with $C_{1-4}$alkyl;

$R_6$ is hydrogen, $C_{1-6}$alkyloxy, Het$^1$, Het$^1$oxy, Het$^2$, Het$^2$oxy, aryl, aryloxy or amino; and in case —A— is other than $C_{1-6}$alkanediyl then R$^6$ may also be $C_{1-6}$alkyl, Het$^1C_{1-4}$alkyl, Het$^1$oxy$C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl; whereby each of the amino groups in the definition of R$_6$ may optionally be substituted with one or two substituents selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl$C_{1-4}$alkyl, Het$^1C_{1-4}$alkyl or Het$^2C_{1-4}$alkyl;

$R_{7a}$ is $C_{1-8}$ alkanediyl; optionally substituted with one or more substituents selected from, halogen, $C_{1-4}$alkylcarbonyl, $C_{1-4}$alkyloxycarbonyl, aryl, arylcarbonyl, aryloxycarbonyl, Het$^1$ or Het$^2$;

$R_{7b}$ is $C_{1-8}$ alkyl; optionally substituted with one or more substituents selected from halogen, $C_{1-4}$alkylcarbonyl, $C_{1-4}$alkyloxycarbonyl, aryl, arylcarbonyl, aryloxycarbonyl, Het$^1$ or Het$^2$;

M is defined by —C(=O)—, —O—C(=O)—, —C(=O)—O—, —CH$_2$—CHOH—, —CHOH—CH$_2$—, —NR$_8$—C(=O)—, —(C=O)—NR$_8$—, —S(=O)$_2$—, —O—, —S—, —O—S(=O)$_2$—, —S(=O)—O—, —NR$_8$—S(=O)$_2$ or —S(=O)$_2$—NR$_8$—;

n is zero or 1.

A particular group of compounds are those compounds of formula (I) wherein one or more of the following restrictions apply:

$R_1$ is hydrogen, Het$^1$, Het$^2$, aryl, Het$^1C_{1-6}$alkyl, Het$^2C_{1-6}$alkyl, aryl$C_{1-6}$alkyl, more in particular, $R_1$ is hydrogen, a saturated or partially unsaturated monocyclic or bicyclic heterocycle having 5 to 8 ring members, which contains one or more heteroatom ring members selected from nitrogen, oxygen or sulfur and which is optionally substituted, phenyl optionally substituted with one or more substituents, an aromatic monocyclic heterocycle having 5 to 6 ring members, which contains one or more heteroatom ring members selected from nitrogen, oxygen or sulfur and which is optionally substituted on one or more carbon atoms, or $C_{1-6}$alkyl substituted with an aromatic monocyclic heterocycle having 5 to 6 ring members, which contains one or more heteroatom ring members selected from nitrogen, oxygen or sulfur and which is optionally substituted on one or more carbon atoms;

$R_2$ is hydrogen;

L is —C(=O)—, —O—C(=O)—, —O—C$_{1-6}$alkanediyl-C(=O)—, more in particular, L is —C(=O)—, —O—C(=O)—, —O—CH$_2$—C(=O)—, whereby in each case the C(=O) group is attached to the NR$_2$ moiety;

$R_3$ is aryl$C_{1-4}$alkyl, in particular, arylmethyl, more in particular phenylmethyl;

$R_4$ is optionally substituted $C_{1-6}$alkyl, in particular $C_{1-6}$alkyl optionally substituted with aryl, Het$^1$, Het$^2$, $C_{3-7}$cycloalkyl or amino optionally mono- or disubstituted where the substituents are selected from $C_{1-4}$alkyl, aryl, Het$^1$ and Het$^2$;

A is $C_{1-6}$alkanediyl, —C(=O)— or $C_{1-6}$alkanediyl-C(=O)—, in particular, A is methylene, 1,2-ethanediyl, 1,3-propanediyl, —C(=O)— or —CH$_2$—C(=O)—;

$R_5$ is hydrogen, $C_{1-6}$alkyl, $Het^1C_{1-6}$alkyl, amino$C_{1-4}$alkyl whereby the amino group may optionally be mono- or di-substituted with $C_{1-4}$alkyl;

$R_6$ is $C_{1-6}$alkyloxy, $Het^1$, aryl, amino; and in case —A— is other than $C_{1-6}$alkanediyl then $R_6$ may also be $C_{1-6}$alkyl, $Het^1C_{1-4}$alkyl, aryloxy$C_{1-4}$alkyl or amino$C_{1-4}$alkyl; whereby each of the amino groups may optionally be substituted; or $R_5$ and —A—$R_6$ taken together with the nitrogen atom to which they are attached may also form $Het^1$;

Haryl is an aromatic mono- or bicyclic heterocycle having 3 to 8 ring members, which contain one or more heteroatoms selected from N, O or S and (i) which Haryl is optionally substituted on one or more carbon atoms by $C_{1-6}$alkyl, $C_{1-6}$alkyloxy, halogen, hydroxy, optionally mono- or disubstituted amino, nitro, cyano, halo-$C_{1-6}$alkyl, carboxyl, $C_{1-6}$alkoxycarbonyl, $C_{1-6}$alkylcarbonyloxy, $C_{3-7}$cycloalkyl, optionally mono- or disubstituted aminocarbonyl, methylthio, methylsulfonyl, aryl, $(R_{7a})_n$—M—$R_{7b}$, $Het^1$ and $Het^2$; whereby the optional substituents on any amino function are independently selected from $R_5$ and —A—$R_6$; and (ii) which Haryl is optionally substituted on a nitrogen atom by hydroxy or —A—$R_6$.

A special group of compounds are those compounds of formula (I) wherein $R_1$ is $Het^1$, aryl, $Het^2C_{1-6}$alkyl; $R_2$ is hydrogen; L is —C(=O)—, —O—C(=O)—, —O—$CH_2$—C(=O)—, whereby in each case the C(=O) group is attached to the $NR_2$ moiety; $R_3$ is phenyl-methyl; and $R_4$ is $C_{1-6}$alkyl.

Another interesting group of compounds are those compounds of formula (I) wherein $R_1$ hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$, $Het^2C_{1-4}$alkyl; wherein $Het^1$ is a saturated or partially unsaturated monocyclic heterocycle having 5 or 6 ring members, which contains one or more heteroatom ring members selected from nitrogen, oxygen or sulfur and which is optionally substituted on one or more carbon atoms.

Another interesting group of compounds are those compounds of formula (I) wherein $R_1$ is aryl$C_{1-6}$alkyl, $Het^1C_{1-6}$alkyl, $Het^2C_{1-6}$alkyl or $Het^1$ having at least 5 carbon atoms.

Another interesting group of compounds are those compounds of formula (I) wherein L is —O—$C_{1-6}$alkanediyl-C(=O)—.

In interesting group of compounds are those compounds of formula (I), wherein the Haryl substituent on the phenyl is in para position vis-à-vis the sulfonamide moiety.

An interesting group of compounds are those compounds of formula (I), wherein the Haryl substituent comprises at least one nitrogen atom, preferably said Haryl substituent comprises at least a nitrogen atom at an alpha position to the Haryl-phenyl bond.

Another interesting group of compounds are those compounds of formula (I) wherein $R_1$ is selected from the group consisting of a disubstituted aryl, a trisubstituted aryl, $Het^2C_{1-6}$alkyl or a $Het^1$; Haryl is monosubstituted or disubstituted; wherein if Haryl is disubstituted at least one substituent is selected from methyl, halogen or amino.

Another interesting group of compounds are those compounds of formula (I), wherein the Haryl moiety is selected from the group comprising thiazolyl, imidazolyl, oxazolyl, oxadiazolyl, pyrazolyl, pyrazinyl, imidazolinonyl, quinolinyl, isoquinolinyl, indolyl, pyridazinyl, pyridinyl, pyrrolyl, pyranyl, pyrimidinyl, furanyl, triazolyl, tetrazolyl, benzofuranyl, benzoxazolyl, isoxazolyl, isothiazolyl, thiadiazolyl, thiophenyl, tetrahydrofurofuranyl, tetrahydropyranofuranyl, benzothiophenyl, carbazolyl, imidazolonyl, oxazolonyl, indolizinyl, triazinyl or quinoxalinyl; whereby the Haryl moiety may be optionally further substituted on one or more ring members; preferably the Haryl moiety is selected from the group consisting of thiazolyl, imidazolyl, oxazolyl, oxadiazolyl, pyrazolyl or pyridinyl, optionally substituted on one or more ring members.

Another interesting group of compounds are those compounds of formula (I), wherein the Haryl moiety is thiazolyl substituted with an optionally mono or disubstituted amino group; preferably said amino group is not substituted or monosubstituted.

Another interesting group of compounds are those compounds of formula (I), wherein the Haryl moiety is pyrazolyl substituted on a nitrogen atom.

Another interesting group of compounds are those compounds of formula (I), wherein the Haryl moiety is oxazolyl substituted with methyl or amino, preferably said substituent is at the 2 position of the oxazolyl moiety.

Another interesting group of compounds are those compounds of formula (I), wherein the Haryl moiety is oxadiazolyl substituted at the 5 position of the oxadiazolyl moiety.

A suitable group of compounds are those compounds of formula (I) as a salt, wherein the salt is selected from trifluoroacetate, fumarate, chloroacetate and methanesulfonate.

An interesting group of compounds are those compounds of formula (I) having a fold resistance, determined according to the methods herein described, in the range of 0.01 to 100 against HIV species having at least one mutation in the HIV protease as compared to the wild type sequence (e.g. genbank accession M38432, K03455, gi 327742) at a position selected from 10, 71 and 84; in particular at least two mutations selected from 10, 71 and 84 are present in the HIV protease; in particular the compounds have a fold resistance in the range of 0.1 to 100, more in particular in the range 0.1 to 50. An interesting group of compounds are compounds No 1-6, 24, 32-33, 35, 23-24, 38-40, 42-44, 46, 48-52, and 57 as disclosed in the present invention.

A suitable group of compounds are compounds No 1-6, 24, 32, 35, 23-24, 38 and 40 as disclosed in the instant invention.

In one aspect $R_5$ may be $C_{2-6}$alkenyl, such —$CH_2$—CH=$CH_2$; aryl such as phenyl or $Het^2$ such as pyridine.

In one aspect the Haryl moiety may also be substituted by $C_{1-6}$alkylcarboxylic acid such as —$CH_2$—$CH_2$—COOH.

The invention also concerns a pharmaceutical composition consisting of a solid dispersion comprising, (a) a compound of formula (I), (b) one or more pharmaceutically acceptable water-soluble polymers. In particular, the compound is selected from compound N° 1-6, 24, 32-33, 35, 23-24, 38-40, 42-44, 46, 48-52, and 57. Conveniently, a water soluble polymer includes hydroxypropylmethylcellulose, polyvinylpyrrolidone copolymer with vinyl acetate (PVP-VA). The invention also relates to a process for the manufacture of a composition comprising at least one compound of formula (I) or exemplified in tables 1 to 6.

The invention further relates to a compound of formula (I) or exemplified in tables 1 to 6 characterized in that said compound is synthesized according to any of schemes 1 to 6. The invention further relates to intermediates as described in the present invention in synthesis of a compound according to formula (I). Interesting intermediates include those of formula B-1, B-2 or K.

The invention further relate to a compound of formula (I) or exemplified in tables 1 to 6 in the manufacture of a medicament for treating, preventing or combating infection or disease associated with retrovirus infection in a mammal, preferably a human.

Compounds having interesting pharmacokinetic properties are those of formula (I), containing at least one substituent independently selected from thiazolyl, imidazolyl and pyridinyl.

The compounds of formula (I) can generally be prepared using procedures analogous to those procedures described in WO 95/06030, WO 96/22287, WO 96/28418, WO 96/28463, WO 96/28464, WO 96/28465 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

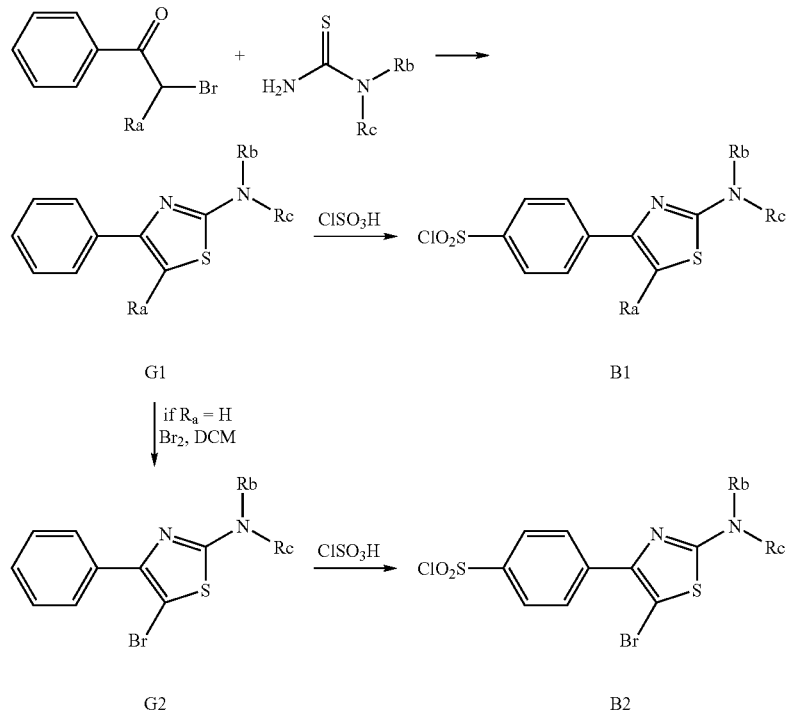

Scheme 1

Reaction of a α-substituted-α-bromoacetophenone with thiourea or substituted thiourea, at elevated temperatures may give gave an intermediate G1. Suitably, this reaction may be performed under refluxing conditions in the presence of DMF (dimethylformamide). This intermediate (G1) may be reacted with chlorosulfonic acid to yield the sulfonyl chloride B-1. For example 2-bromopropiophenone may be reacted with thiourea to yield 2-amino-5-methyl-4-phenylthiazole, which can be further transformed to 4-(2-amino-5-methylthiazol-4-yl)phenyl sulfonyl chloride.

When phenylacetylbromide was used to yield intermediate G1, this latter was first brominated using techniques known in the art, before reaction with chlorosulfonic acid, yielding for example 4-(2-amino-5-bromothiazol-4-yl)phenyl sulfonyl chloride. $R_a$, $R_b$ and $R_c$ are each independently Haryl substituents.

Scheme 2

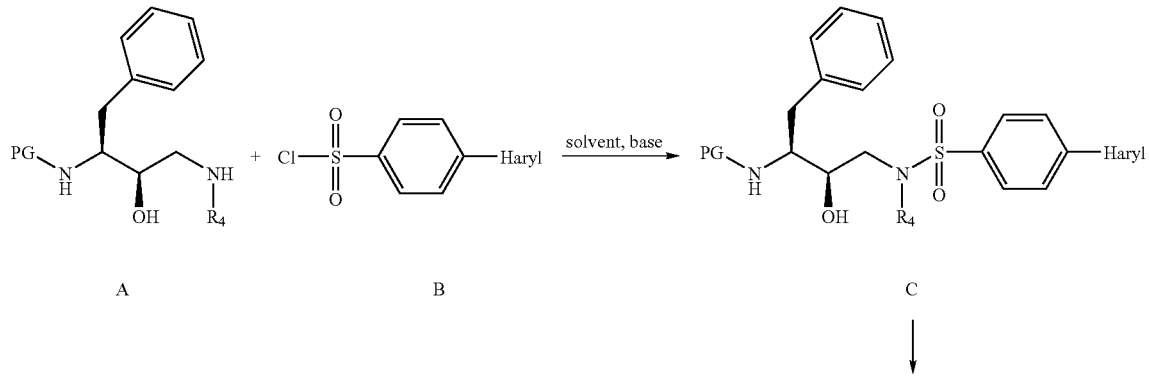

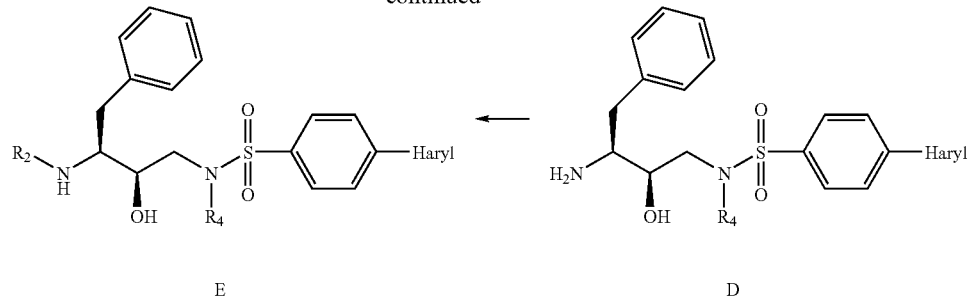

E          D

Intermediate C may be prepared by reacting at low temperature intermediate A, obtained according to the procedure described in patent WO97/18205, with intermediate B in a reaction-inert solvent in the presence of a base. For example, the reaction may be performed at about 0° C. in dichloromethane the presence triethylamine ($Et_3N$).

The aminoterminal protective group in the intermediates may be a protective group (PG) known in the art such as tert-butyloxycarbonyl group. This protective group may conveniently be replaced by another suitable protective group such as phtalimido, dibenzyl or benzyloxycarbonyl. Intermediate C may be deprotected using an acid, such as trifluoroacetic acid, in a suitable solvent such as dichloromethane, yielding an intermediate D. In one embodiment, a 4-(2-substituted amino-5-bromothiazol-4-yl)phenyl sulfonamide derivative C may be debrominated by catalytic hydrogenation for example, prior to protective group removal. The aminoterminal group of intermediate D may subsequently be substituted by procedures known in the art to generate E. Alternatively, intermediates may be deprotected with a strong acid such as hydrochloric acid in isopropanol, in a suitable solvent such as a mixture of ethanol and dioxane. In a preferred embodiment the protecting group may be selected from Fmoc, acetyl, tert-butyloxycarbonyl, benzyloxycarbonyl-, and dibenzyl-.

Scheme 3

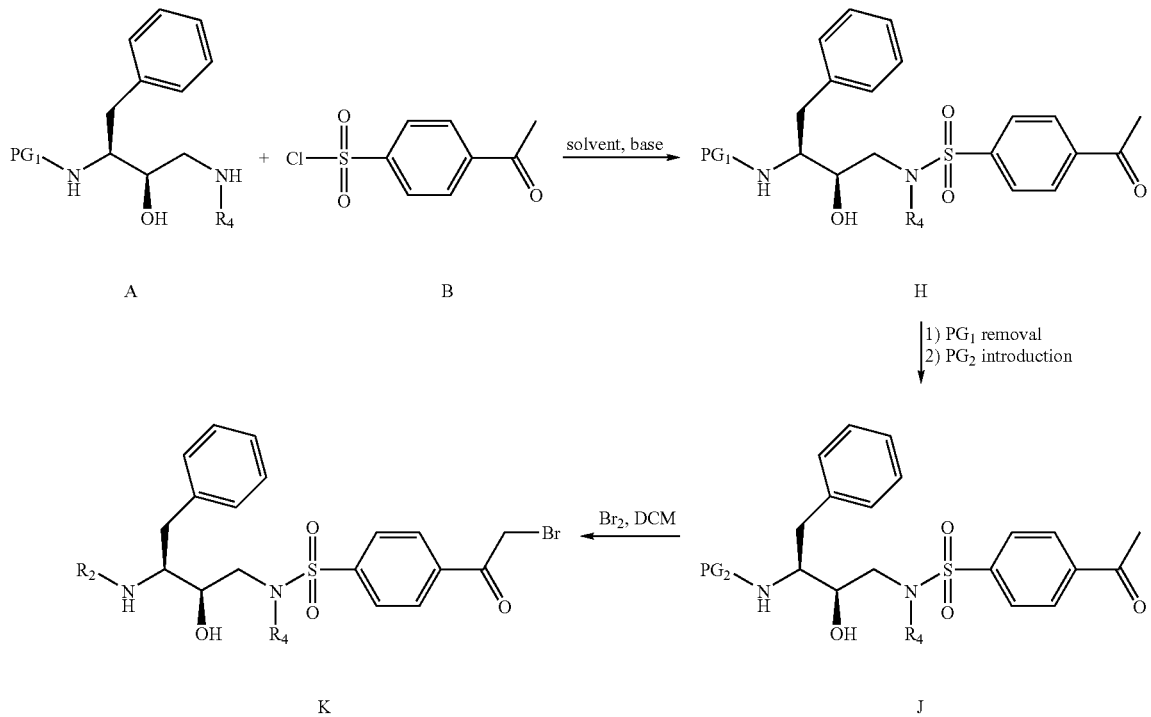

Intermediate A may be generated as described in Synthesis 2. A may be reacted with 4-acetyl-phenylsulfonyl chloride to generate H. Suitable conditions for this reaction include a polar aprotic solvent such as dichlormethane and the use of a base such as $Et_3N$. The protecting group may be removed and exchanged for another protecting group and the acetyl moiety of the phenyl ring is halogenated using techniques known in the art such as $Br_2$. The exchange of protecting group may improve the bromination reaction. The heterocycle on the phenyl-moiety may be introduced using reactions as described in synthesis 1. Following introduction of said heterocycle, the aminoterminal group may be deprotected under conditions known in the art and the free aminomoiety may subsequently be substituted using procedures known to the person skilled in the art.

Synthesis scheme 3.1

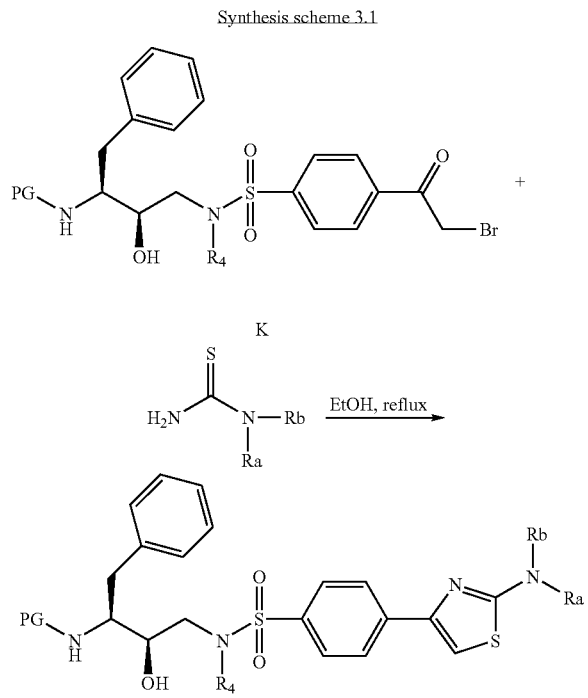

Examples of this reaction include the phenylsubstituted thiazoles. Thiourea or optionally substituted thiourea may be reacted with intermediate K to generate 2-amino-substituted thiazole derivatives. The reaction may be performed in organic solvents at elevated temperatures. For example, reaction conditions may include ethanol under refluxing conditions. $R_a$ and $R_b$ are each independently Haryl substituents. In another example thioamides may be reacted with K to yield 2-substituted thiazoles.

Synthesis scheme 3.2

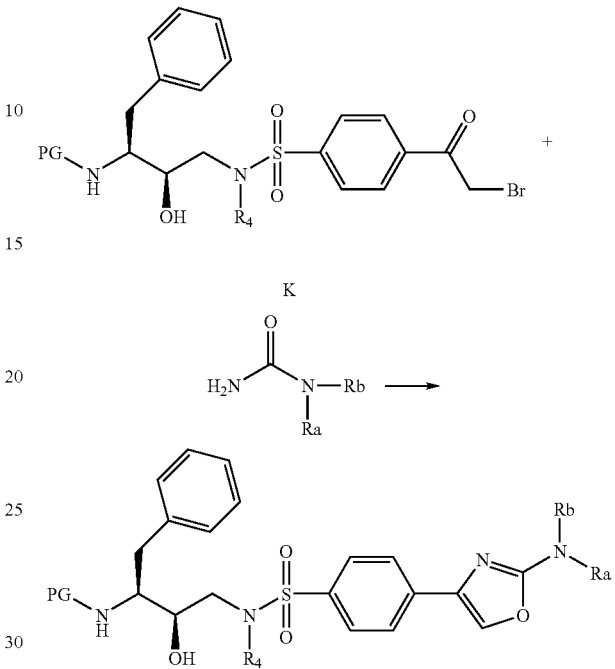

Oxazoles may be prepared starting from K which may be reacted with urea or substituted urea molecules to obtain 2-aminosubstituted oxazoles. The reaction may be performed in organic solvents at elevated temperatures. For example, reaction conditions include ethanol under refluxing conditions. $R_a$ and $R_b$ are each independently Haryl substituents. 2-alkyl substituted oxazoles are prepared by reacting K with amides of formula R—C(=O)—$NH_2$, wherein R is a Haryl substituent.

Synthesis scheme 3.3

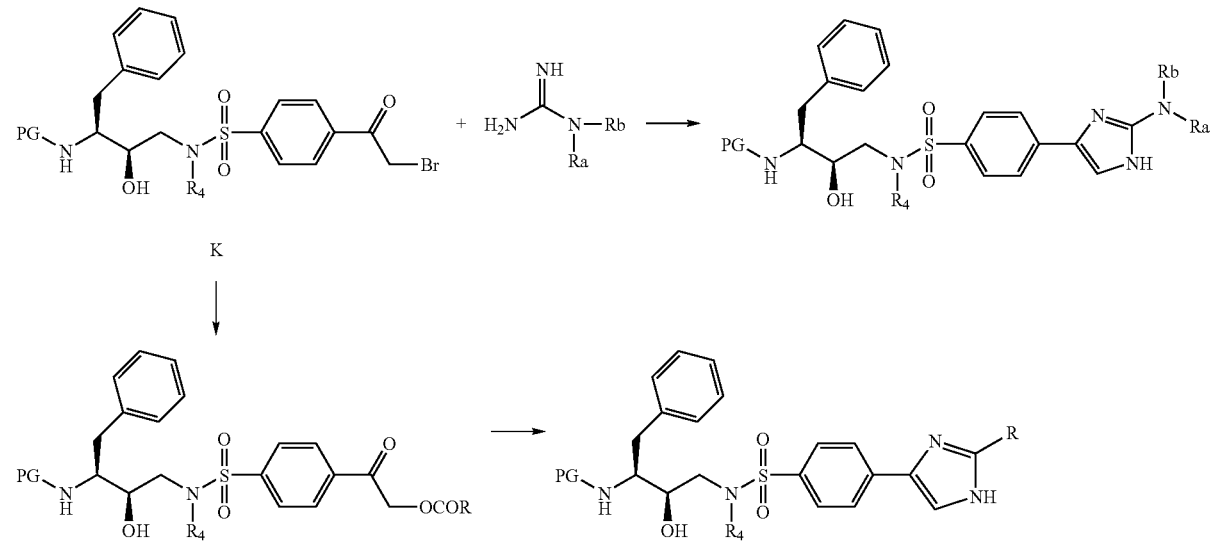

Imidazoles may be prepared by reacting guanidino-derivatives with intermediate K. This reaction procedure yields 2-aminosubstituted-imidazole derivatives. In another approach K may be reacted with amidines to generate 2-substituted imidazoles. The reaction can be performed in organic solvents at elevated temperatures, for example in the presence of THF (tetrahydrofurane) under refluxing conditions.

In one embodiment the imine function of the guanidine-derivative may be incorporated in a cycle, such as 2-aminothiazole. This may yield e.g. imidazo[2,1-b]thiazole. In one embodiment the intermediate K may be reacted with salts of alkylcarboxylic acids to yield acetyl oxycarbonyl substituents. This reaction may be performed at elevated temperatures in organic solvents, for example at about 60° C. in DMF (dimethylformamide). The obtained intermediate may be further reacted with ammonia acetate to yield 2-substituted imidazoles. R. $R_a$ and $R_b$ are each independently Haryl substituents.

Synthesis scheme 3.4

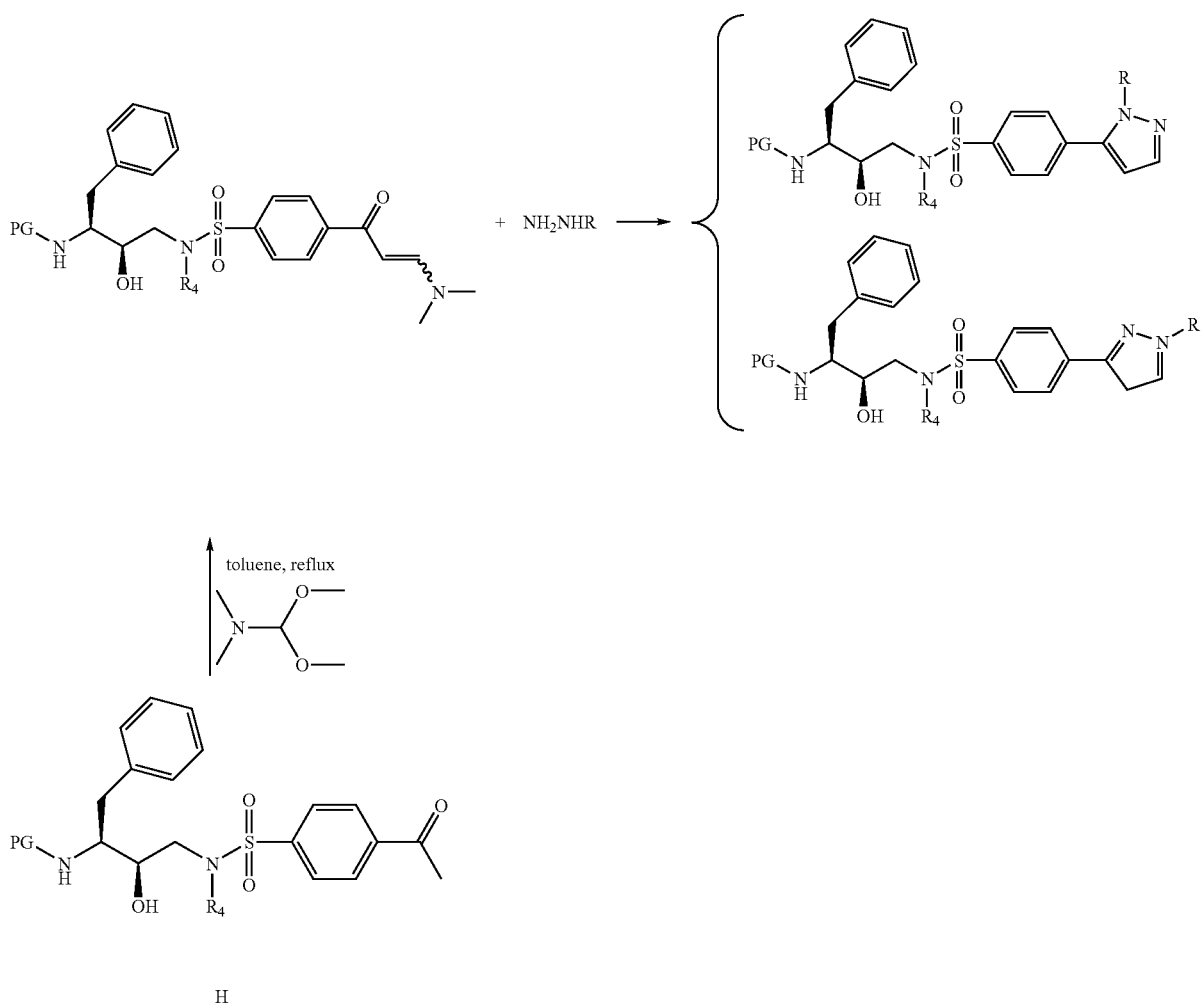

Intermediate H may be reacted with N,N-dimethylformamide dimethyl acetal, in an organic solvent such as toluene. This reaction may be performed at elevated temperatures, to yield an intermediate as a mixture of cis and trans isomers. This latter intermediate may be further reacted with hydrazine or substituted hydrazine. The reaction may be performed at elevated temperatures in an organic solvent in the presence of a base. For example, the reaction may be performed in the presence of a base such as potassium carbonate, with ethanol as a solvent, under reflux conditions. The obtained product is a mixture of isomers. R is an Haryl substituent.

Synthesis scheme 4

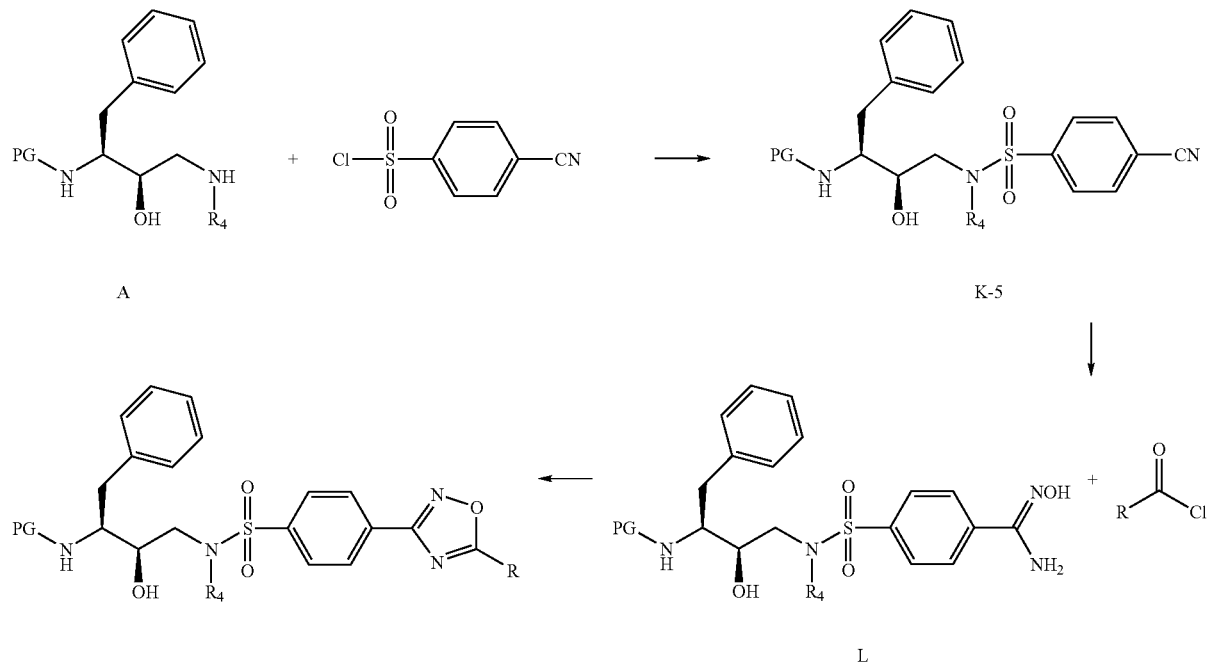

A may be reacted with 4-cyano-phenylsulfonyl chloride to give intermediate K-5. The reaction may be performed at lower temperatures in organic solvents under alkaline conditions. For example, the reagents may be mixed at about 0° C. in dichloromethane (DCM) in the presence of triethylamine. The temperature may then be allowed to increase to about room temperature. Intermediate K-5 may be further reacted with hydroxylamine to produce intermediate L. For example, intermediate K-5 may be reacted with hydroxylamine in ethanol in the presence of a base such as potassium carbonate under elevated temperatures. Refluxing conditions may be used.

(5-R-oxadiazol-3-yl)phenylsulfonamide derivatives may be obtained after reaction of intermediate L with an acyl chloride of formula RC(=O)Cl. In one embodiment, the latter reaction may be performed with pyridine as a solvent at elevated temperatures, for example at about 110° C. R is an Haryl substituent.

The amino-protecting group may be removed following the generation of the heterocycle-phenyl moiety using conditions known in the art. Subsequently, the amino-moiety may be substituted with other groups using conditions known in the art. A preferred amino-substituent may be a bis-THF ester moiety.

Synthesis scheme 5

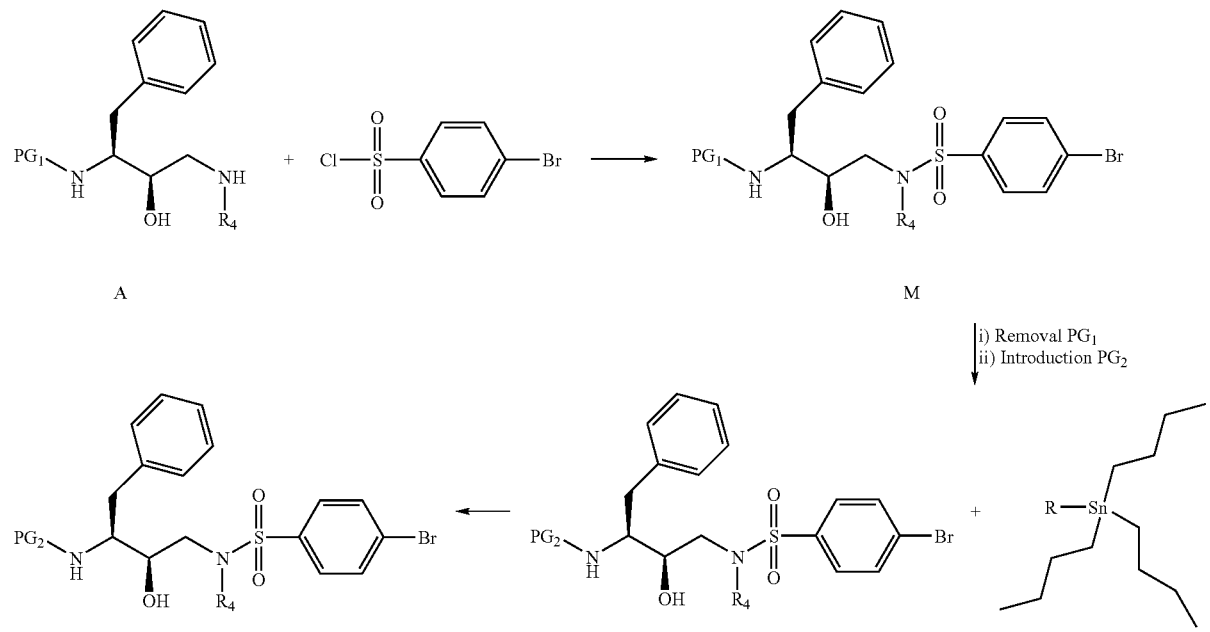

Intermediate A may be reacted with 4-bromo-phenylsulfonyl chloride to yield intermediate M. The reaction may be performed at lower temperatures in organic solvents under alkaline conditions. For example, the reagents may be mixed at about 0° C. in dichloromethane in the presence of triethylamine. The temperature may then be allowed to increase to about room temperature. The protecting group of intermediate M may be exchanged for another protecting group. For example, $PG_1$ is a boc group and $PG_2$ is a bis-tetrahydrofurane group. Intermediate M may be further reacted with a tributyltin derivative of formula $RSn(nBu)_3$, in organic solvents in the presence of a base and catalyst at elevated temperature. For example, the reaction may be performed in dioxane, in the presence of a base such as triethylamine, and a catalyst such as [1,1'-bis(diphenylphosphino) ferrocene]palladium(II) dichloromethane adduct, at about 85° C. R is Haryl optionally substituted as defined above.

In one embodiment, the protective group may be replaced by another one, preferably a bisTHF ester, prior to the reaction with a tributyltin derivative.

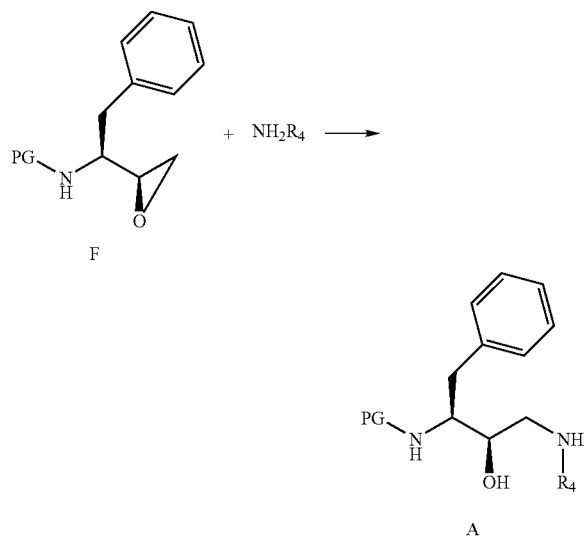

Scheme 6

Intermediate A may be prepared by reacting compound F with an amine, in a suitable solvent such as isopropanol. It is clear from scheme 6 that the stereochemistry of intermediate F, determines the stereochemistry of intermediate A.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), Kaposi's syndrome, thrombocytopenia purpurea, as well as chronic CNS diseases caused by retroviruses, such as, for example HIV mediated dementia and multiple sclerosis. The compounds of the present invention are also useful in case of actual or potential exposure to HIV, tropical parapesis, and also anti-HIV antibody positive and HIV-positive conditions, including such conditions in asymptomatic patiens.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, such as HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

The compounds of this invention may be employed in a conventional manner for the treatment of viruses, such as HIV and HTLV, which depend on aspartyl proteases for obligatory events in their life cycle. Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, and in particular, other human aspartyl proteases, including renin and aspartyl proteases that process endothelin precursors.

In one embodiment, the invention relates to the use of a compound of formula (I) or any subgroup thereof in the manufacture of a medicament for treating, preventing or combating infection or disease associated with multi-drug resistant retrovirus infection in a mammal, such as HIV-1 infection. Thus, the invention also relates to a method of treating a retroviral infection, or a disease associated with multi-drug resistant retrovirus infection comprising administering to a mammal in need thereof an effective amount of a compound of formula (I) or a subgroup thereof. Preventing or prevention is meant to include prophylaxis of HIV infection and prophylaxis of the evolution of HIV infection to AIDS.

In another embodiment, the present invention relates to the use of formula (I) or any subgroup thereof in the manufacture of a medicament for inhibiting a protease of a multi-drug resistant retrovirus in a mammal infected with said retrovirus, in particular HIV-1 retrovirus.

In another embodiment, the present invention relates to the use of formula (I) or any subgroup thereof in the manufacture of a medicament for inhibiting multi-drug resistant retroviral replication, in particular HIV-1 replication.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretro-viral compound, as a combined preparation for simultaneous, separate or sequential use in the prevention or treatment of retroviral infections, in particular, in the treatment of infections with multi-drug resistant retroviruses. Thus, to combat, prevent or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK 779, T-22, ALX40-4C; SHC-C(SCH351125), SHC-D, PRO-140, RPR103611; RT inhibitors, such as, for example, foscarnet and prodrugs; nucleoside RTIs, such as, for example, AZT, 3TC, DDC, DD1, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC442, UC 781, UC 782, Capravirine, QM96521, GW420867X, DPC 961, DPC963, DPC082, DPC083, TMC-125, calanolide A, SJ-3366, TSAO, 4"-deaminated TSA0, MV150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908 (fosamprenavir), ritonavir, nelfinavir, saquinavir, indinavir, lopinavir, palinavir, BMS 186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690; glycosylation inhibitors, such as, for example, castanospermine, deoxynojirimycine; entry inhibitors CGP64222.

The compounds of this invention may be administered as single agents or in combination with other agents. Combination therapies may exert an additive or synergistic effect in inhibiting HIV replication because each compound of the combination may act on a different site of HIV replication or may act on a different site of the target protein. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single antiretroviral agent therapies, while not interfering with the anti-retroviral activity of those agents. These combinations reduce potential of resistance to single agent therapies, while minimizing any associated toxicity. These combinations may also increase the efficacy of the conventional agent without increasing the associated toxicity. Examples of combinations include multiple combinations comprising from 2 to 6 agents. In one embodiment, the combination may provide a synergistic effect, whereby viral infectivity and its associated symptoms may be prevented, substantially reduced, or eliminated completely. For each combination, the combination index (CI) may determined according to a method described by Chou and Talalay (Adv. Enzyme Regul. 22: 27-55, 1984). A CI value from about 0.8 to about 1.2 reflects additive inhibition of combined compounds, a value below 0.8 indicates a synergy between two molecules, whereas a value greater than 1.2 is indicative of antagonism.

The compounds of the present invention may also be administered in combination with immunomodulators (e.g., bropirimine, anti-human alpha interferon antibody, IL-2, methionine enkephalin, interferon alpha, HE-2000 and naltrexone), antibodies (e.g. monoclonal antibody Hu-5A8), vaccines (e.g. AG-1661, Aidsvax B/B), antibiotics (e.g., pentamidine isothiorate) cytokines (e.g. Th2), modulators of cytokines, chemokines or the receptors thereof (e.g. CCR5) or hormones (e.g. growth hormone, filgrastim) to ameliorate, combat, or eliminate HIV infection and its symptoms. Such combination therapy in different formulations, may be administered simultaneously, separately or sequentially. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Other useful inhibitors of cytochrome $P_{450}$ include ketoconazole, cimetidine or bergamottin. Another group of cytochrome $P_{450}$ inhibitors include itraconazole, clarithromycine, erythromycine, nefazodone, delavirdine or troleandomycine. Said modulator may also be an HIV protease inhibitor and is for example selected from the group comprising indinavir, nelfinavir, saquinavir, amprenavir, lopinavir, lasinavir, palinavir, telinavir, tipranavir, mozenavir, atazanavir. Such combination therapy in different formulations, may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy $C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, PCT application No. PCT/EP98/01773, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bio-available to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother*, 1998; 42(2):269-276, incorporated by reference).

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl; or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of formula (I) in the case of administration to a patient approximately 75 kg in weight is 1 mg to 1 g, preferably 3 mg to 0.5 g. The dose can be administered in the form of an individual dose, or divided into several, e.g. two, three, or four, individual doses.

The following tables list the compounds of formula (I) which were prepared following one of the above reaction schemes.

EXPERIMENTAL PART

1. Preparation of the Compounds of Formula (B) and their Intermediates

Example 1

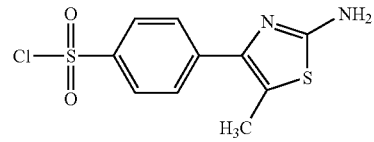

A mixture of 2 g of 2-bromopropiophenone and 0.71 g of thiourea in 50 mL of ethanol was refluxed overnight. After solvent evaporation, the residue was redissolved in 50 mL of ethyl acetate and treated by 50 mL of a 2% sodium carbonate solution in water. The organic layer was dried and evaporated to yield 1.77 g (99%) of intermediate G 5-methyl-4-phenyl-2-thiazolamine. Mass spectral data: m/z=191 (M+H).

2.11 g of chlorosulfonic acid was added to 0.77 g of intermediate G in 20 mL of DCM (dichloromethane). The mixture was heated to about 50° C. during 1 hour. After cooling down to room temperature, the mixture was poured on ice and extracted with ethyl acetate. The organic layer was separated, dried over MgSO$_4$ and evaporated to yield 0.74 g (63%) of compound B 4-(2-amino-5-methylthiazol-4-yl)benzene sulfonyl-chloride. Mass spectral data: m/z=289 (M+H).

Example 2

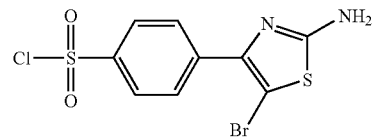

A mixture of 2 g of phenacylbromide and 0.76 g of thiourea in 50 mL ethanol was refluxed overnight. After solvent evaporation, the residue was redissolved in 50 mL DCM and treated by 50 mL of a 2% sodium carbonate solution in water. The organic layer was dried and evaporated to yield 1.45 g (82%) of 4-phenyl-2-thiazolamine (intermediate p. Mass spectral data: m/z=177 (M+H).

0.71 g of Br$_2$ was added to 0.77 g of intermediate G in 10 mL of DCM, at 0° C. The reaction mixture was allowed to warm up to room temperature and was stirred during 30 minutes. A 2% solution of Na₂CO₃ in water was then added. The organic layer was separated, dried over MgSO₄ and evaporated to yield 1.07 g (95%) of intermediate N 5-bromo-4-phenyl-2-thiazolamine. Mass spectral data: m/z=255 (M+H).

1.2 mL of chlorosulfonic acid was added to 0.75 g of intermediate N in 5 mL of DCM. The mixture was heated to about 50° C. during 2 hours. After cooling down to room temperature, the mixture was poured on ice and extracted with ethyl acetate. After removal of the organic phase, a saturated solution of Na₂CO₃ in water was added to the aqueous phase and extracted with ethyl acetate. This organic layer was separated, dried over MgSO₄ and evaporated to yield 0.67 g of intermediate O 4-(2-amino-5-bromothiazol-4-yl) benzene sulfonylchloride. Mass spectral data: m/z=394 (M+H).

2. Preparation of the Compounds of Formula (C) and their Intermediates

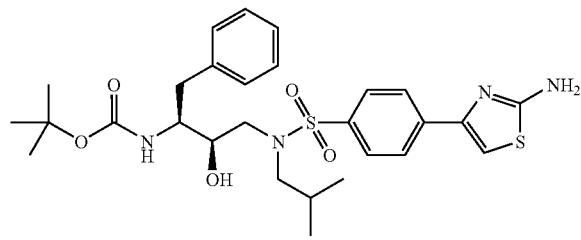

A mixture of 0.48 g of intermediate A [2R-hydroxy-3-[(2-methylpropyl)amino]-1S-(phenylmethyl)propyl]carbamic acid, 1,1-dimethylethyl ester (PG=Boc) and 0.36 g of triethylamine in 25 ml of dichloromethane was stirred at about 0° C. Then 0.67 g of intermediate O, was added and the reaction mixture was stirred during 2 h at room temperature. After washing with water, the organic layer was separated, dried over MgSO₄ and the solvent evaporated, yielding 1.06 g (100%) of intermediate P [(1S,2R)-3-[N-[4-(2-amino-5-bromothiazol-4-yl)phenylsulfonyl]-N-(2-methylpropyl) amino]-2-hydroxy-1-(phenylmethyl)propyl]carbamic acid, 1,1-dimethylethyl ester. Mass spectral data: m/z=653 (M+H).

Pd/C and hydrogen was added to a mixture of 1.06 g of intermediate P in 25 mL of methano. The reaction mixture was stirred overnight, then filtered over decalite and evaporated to yield 0.94 g of compound C [(1S,2R)-3-[N-[4-(2-amino-thiazol-4-yl)phenylsulfonyl]-N-(2-methylpropyl) amino]-2-hydroxy-1-(phenylmethyl)propyl]carbamic acid, 1,1-dimethylethyl ester. Mass spectral data: m/z=575 (M+H).

Example 3

Preparation of the Compounds of Formula (K-1) and their Intermediates

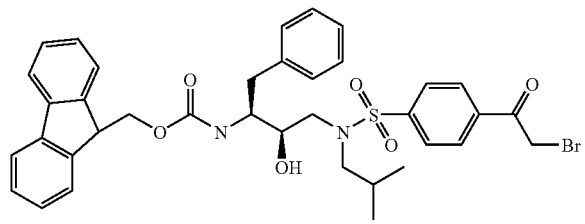

A mixture of 20 g of intermediate A (PG=Boc) and 6.61 g of triethylamine in 500 ml of dichloromethane was stirred at about 0° C. Then 13.6 g of 4-acetylbenzene sulfonyl chloride, was added and the reaction mixture stirred during 3 h at room temperature. After washing with water, the organic layer was separated, dried over MgSO₄ and the solvent evaporated, yielding 30.9 g (100%) of intermediate H [(1S,2R)-3-[N-(4-acetylphenylsulfonyl)-N-(2-methylpropyl)amino]-2-hydroxy-1-(phenylmethyl)propyl]carbamic acid, 1,1-dimethylethyl ester. Mass spectral data: m/z=519 (M+H).

100 ml of HCl (5 to 6 N in isopropanol) was added to 30.9 g of intermediate H in 400 ml of dichloromethane. The reaction was stirred at room temperature for 4 hours. After solvent evaporation, intermediate I was obtained as an HCl salt N-[(2R,3S)-3-amino-2-hydroxyphenylbutyl]-N-(2-methylpropyl)-4-acetylphenylsulfonamide, hydrochloride (26.9 g, 99%)(t). Mass spectral data: m/z=419 (M+H).

2.85 g of 9-fluorenylmethylchloroformate Fmoc-Cl and 2.23 g of triethylamine were added to 5 g of intermediate I in 150 mL of dichloromethane. The reaction mixture was stirred overnight at room temperature, then washed with water, dried over MgSO₄ and evaporated to yield 7.2 g of intermediate J-1 [(1S,2R)-3-[N-(4-acetylphenylsulfonyl)-N-(2-methylpropyl)amino]-2-hydroxy-1-(phenylmethyl)propyl]carbamic acid, 9-fluorenylmethylester. Mass spectral data: m/Z=641 (M+H).

2.11 g bromine was added to 6.5 g of intermediate J-1 in 200 mL of dichloromethane. The reaction mixture was stirred at room temperature during 1 hour, then washed with a saturated solution of NaHCO₃ in water, dried over MgSO₄ and evaporated. The crude product was purified on silica gel eluting with 20% ethyl acetate in hexane, yielding 3.6 g (50%) of intermediate K-1 [(1S,2R)-3-[N-[(4-bromoacetylphenyl)sulfonyl]-N-(2-methylpropyl)amino]-2-hydroxy-1-(phenylmethyl)propyl]carbamic acid, 9-fluorenylmethylester. Mass spectral data: m/z=719 (M+H).

Example 4

Preparation of the Compounds of Formula (K-2) and their Intermediates

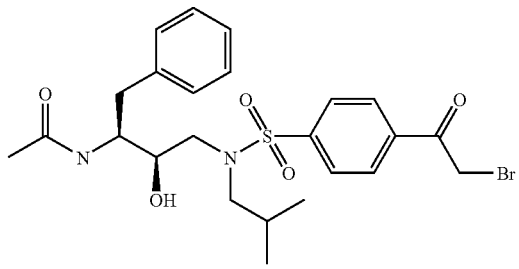

3.33 g triethylamine was added to 5 g of intermediate I in 100 mL of dichloromethane. After cooling to about 0° C., 0.94 g of acetylchloride was added. The reaction mixture was stirred overnight at room temperature, then washed with water, dried over MgSO₄ and evaporated to yield 5 g (99%) of intermediate J-2 [(1S,2R)-3-[N-(4-acetylphenyl sulfonyl)-N-(2-methylpropyl)amino]-2-hydroxy-1-(phenylmethyl)propyl]acetamide. Mass spectral data: m/z=461 (M+H).

To 10 g of intermediate J-2 in 250 mL of dichloromethane was added dropwise a solution of bromine (3.78 g in 20 mL of dichloromethane) over one hour. After overnight stirring at room temperature, 1 mL of HCl 12 N was added. The reaction mixture was stirred during 3 days, then washed with a saturated solution of NaHCO₃ in water, dried over MgSO₄ and evaporated. The crude product was purified on silica gel eluting with 60% ethyl acetate in hexane, yielding 5.9 g (50%) of intermediate K-2 [(1S,2R)-3-[N-[4-(bromoacetyl)phenylsulfonyl]-N-(2-methylpropyl)amino]-2-hydroxy-1-(phenylmethyl)propyl]acetamide. Mass spectral data: m/z=539 (M+H).

Example 5

Preparation of the Compounds of Formula (K-3) and their Intermediates

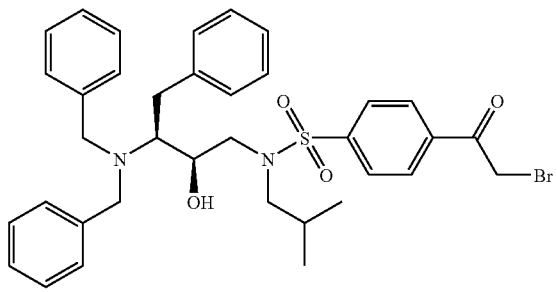

A mixture of 8.3 g of intermediate A (PG=diBenzyl), [(1R,2S)-2-[bis(phenylmethyl) amino]-1-[(2-methylpropyl) amino]methyl]benzenepropanol, and 2.12 g of triethylamine in 200 ml of dichloromethane (DCM) was stirred at 0° C. Then 4.5 g of 4-acetylbenzene sulfonyl chloride dissolved in 100 mL of DCM, were added dropwise and the reaction mixture stirred overnight at room temperature. After washing with water, the organic layer was separated, dried over MgSO$_4$ and the solvent evaporated, yielding 12.07 g (100%) of intermediate H N-[(2R,3S)-3-(N',N'-dibenzyl)amino-2-hydroxy-4-phenylbutyl]-N-(2-methylpropyl)$_4$-acetylphenylsulfonamide. Mass spectral data: m/z=599 (M+H).

2.40 g of bromine and 0.6 g of acetic acid was added to a mixture of 5 g of intermediate H in 100 mL dichloromethane. The reaction mixture was stirred at room temperature during 6 hours, then 0.25 mL bromine were added and the mixture stirred for 1 hour. The mixture was then washed with a saturated solution of NaHCO$_3$ in water, dried over MgSO$_4$ and evaporated. The crude product was purified on silica gel eluting with 20% hexane in DCM, yielding 2.25 g (40%) of intermediate K-3 N-[(2R,3S)-3-(N',N'-dibenzyl)amino-2-hydroxy-4-phenylbutyl]-N-(2-methylpropyl)-4-bromoacetylphenylsulfonamide. Mass spectral data: m/z=679 (M+H).

Example 6

Preparation of the Compounds of Formula (K4) and their Intermediates

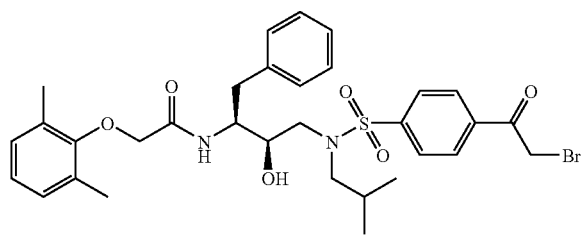

2.67 g of triethylamine, 2.38 g of (2,6-dimethylphenoxy) acetic acid, 1.78 g of 1-hydroxybenzotriazole and 2.77 g of 1-(3-dimethylaminopropyl)-3-ethylcarbodiimide hydrochloride were added to 6 g of intermediate I in 200 mL of dichloromethane. The mixture was stirred overnight, washed with water, dried over MgSO$_4$ and concentrated to yield 7.67 g (100%) of the desired intermediate H-4 [(1S,2R)-3-[N-(4-acetylphenylsulfonyl)-N-(2-methylpropyl)amino]-2-hydroxy-1-(phenylmethyl)-propyl]-(2,6-dimethylphenoxy)acetamide. Mass spectral data: m/z=581 (M+H).

To a mixture of 4 g of the previous intermediate in 100 mL of dichloromethane was added dropwise a solution of bromine (1.66 g in 20 mL of dichloromethane) over 15 minutes. The reaction mixture was stirred during 2.5 hours, then washed with a saturated solution of NaHCO$_3$ in water, dried over MgSO$_4$ and evaporated. The crude product was purified on silica gel eluting with 3% ethyl acetate in DCM, yielding 2 g (45%) of intermediate K4 [(1S,2R)-3-[N-(4-bromoacetylphenylsulfonyl)-N-(2-methylpropyl)amino]-2-hydroxy-1-(phenylmethyl)propyl]-(2,6-dimethylphenoxy)acetamide. Mass spectral data: m/z=659 (M+H).

Example 7

Synthesis of Pyrazoles

Preparation of Compound 24

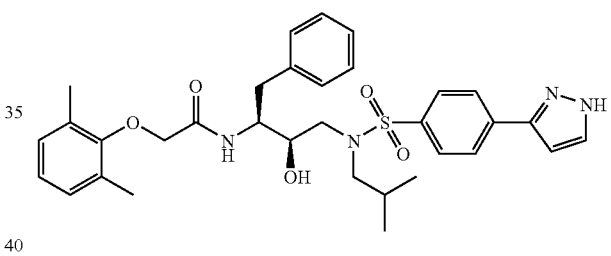

To 2 g of intermediate H-4 in 100 mL toluene was added 0.45 g of N,N-Dimethylformamide dimethylacetal. The mixture was refluxed overnight, then 0.2 g of N,N-Dimethylformamide dimethylacetal was added again. After overnight stirring under reflux, the same procedure was repeated (0.2 g of reactant and overnight reflux). The mixture was then concentrated and the crude product was purified on silica gel eluting with 40% ethyl acetate in hexane. The fractions comprising the desired compound were collected and evaporated. The residue was then dissolved in 100 mL of methanol containing 1.43 g of potassium carbonate. The mixture was stirred during 1 hour at room temperature and finally evaporated to yield 1.74 g of the intermediate I-4, as a mixture of two isomers cis and trans [(1S,2R)-3-[N-[4-(3-(dimethylamino)-1-oxo-2-propenyl)phenylsulfonyl]-N-(2-methyl propyl)amino]-2-hydroxy-1-(phenylmethyl)-propyl]-(2,6-dimethylphenoxy)acetamide. Mass spectral data: m/z=636 (M+H).

To 95 mg of intermediate I-4 in 5 mL ethanol was added 62 mg of potassium carbonate and 10 mg of hydrazine hydrochloride. The mixture was refluxed during 18 hour and evaporated. The crude mixture was purified by preparative HPLC, yielding 21 mg (23%) of the desired pyrazole [(1S,2R)-2-hydroxy-3-[N-(2-methylpropyl)-N-(4-pyrazol-3(5)-ylphenylsulfonyl)-amino]-1-(phenylmethyl)propyl]-(2,6-dimethyl phenoxy) acetamide. Mass spectral data: m/z=605 (M+H).

Example 8

Synthesis of Thiazoles Preparation of the Compounds of Formula (L-1)

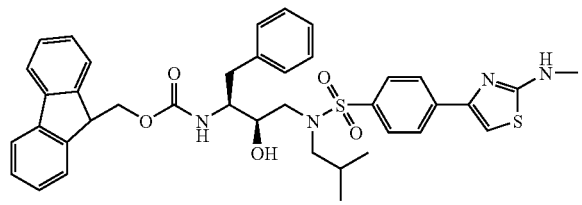

To 0.5 g of intermediate K-1 in 40 mL ethanol was added 0.063 g of methylthiourea. The reaction mixture was heated to reflux during 1 hour and evaporated, yielding 0.55 g of intermediate L-1 [(1S,2R)-2-hydroxy-3-[N-[4-(2-methylaminothiazo-4-yl)phenylsulfonyl]-N-(2-methylpropyl)amino]-1-(phenylmethyl)propyl]carbamic acid, 9-fluorenylmethylester. Mass spectral data: m/z=645 (M+H).

Example 9

Preparation of the Compounds of Formula (M-1)

Preparation of Compound 9

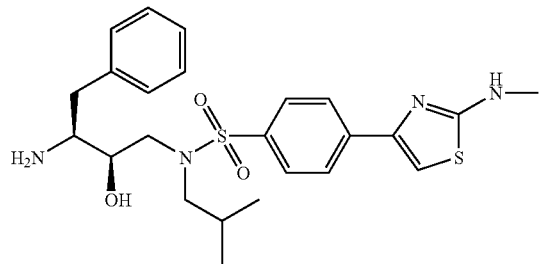

To 0.49 g intermediate L-1 in 40 mL DMF was added 0.59 g of piperidine. The reaction mixture was stirred at room temperature during 2 hours. After solvent evaporation, the crude compound was purified on silica gel eluting with 2% methanol in dichloromethane until 4% methanol, yielding 0.21 g (62%) of intermediate M-1 N-[(2R,3S)-3-amino-2-hydroxy-4-phenylbutyl]-N-(2-methylpropyl)-[4-(2-methylaminothiazol-4-yl)phenyl]sulfonamide. Mass spectral data: m/z=489 (M+H).

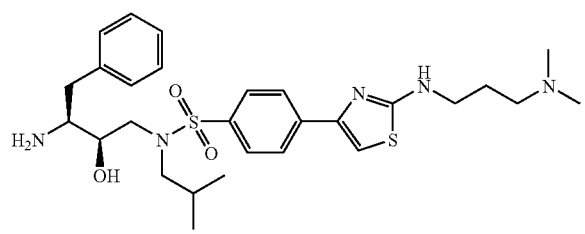

To 0.74 mL of benzoyl isothiocyanate in 30 mL tetrahydrofuran was added 0.64 mL N,N-dimethylaminopropylamine. The mixture was stirred at room temperature overnight. 0.6 mL of a 50% solution of sodium hydroxide in water was then added and the mixture heated to reflux overnight. The reaction mixture was then filtered and the filtrate evaporated. The residue thus obtained was redissolved in 30 mL of DCM, washed with a saturated solution of sodium bicarbonate in water, dried over MgSO$_4$ and evaporated to yield 0.46 g (57%) of the intermediate thiourea (3-dimethylamino-propyl)thiourea. Mass spectral data: m/z=162 (M+H).

To 0.14 g intermediate K-1 in 40 mL ethanol was added 0.063 g of the previous intermediate thiourea. The reaction mixture was heated to reflux overnight and evaporated. 0.06 g (56%) of intermediate L-1 N-[(2R,3S)-3-amino-2-hydroxy-4-phenylbutyl]-N-(2-methylpropyl)-[4-[2-(3-dimethylaminopropylamino)thiazol-4-yl]phenyl]sulfonamide was obtained after purification by preparative HPLC. Mass spectral data: m/z=560 (M+H).

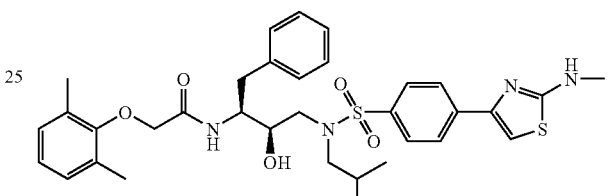

To 0.1 g of intermediate K-4 in 2 mL ethanol was added 13.7 mg methylthiourea. The reaction mixture was heated to reflux during 1 hour and evaporated. The crude compound was purified by preparative HPLC, yielding 50 mg of final compound [(1S,2R)-2-hydroxy-3-[N-[4-[2-(methylamino)thiazol-4-yl]phenylsulfonyl]-N-(2-methyl propyl)amino]-1-(phenylmethyl)propyl]-(2,6-dimethylphenoxy)acetamide. Mass spectral data: m/z=651 (M+H).

Example 10

Synthesis of Oxazoles

Preparation of the Compounds of Formula (L-2)

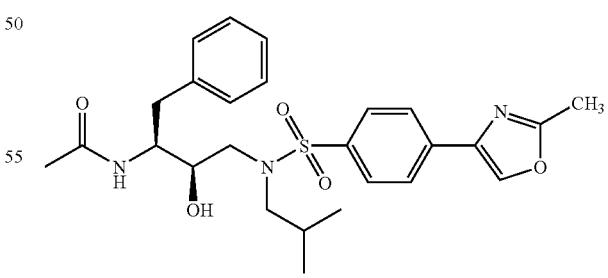

To 0.2 g of intermediate K-2 in 10 mL dimethylformamide was added 0.26 g acetamide. The reaction mixture was heated to 140° C. during 2 hour. After solvent evaporation, the crude compound was purified on silica gel eluting with 5% methanol in dichloromethane, yielding 0.09 g (45%) of intermediate L-2 [(1S,2R)-2-hydroxy-3-[N-[4-(2-methyloxazol-4-yl)

phenylsulfonyl]-N-(2-methylpropyl)amino]-1-(phenylmethyl)propyl]acetamide. Mass spectral data: m/z=500 (M+H).

Example 11

Preparation of the Compounds of Formula (M-2)

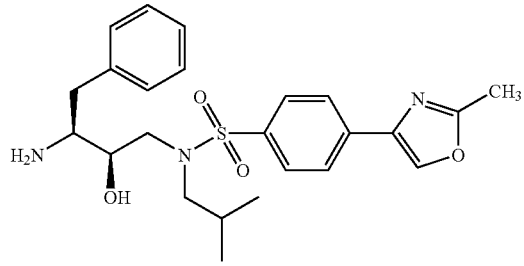

0.09 g of intermediate L-2 were dissolved in 10 mL of HCl 5 N in isopropanol. The reaction mixture was heated at 70° C. overnight. After solvent evaporation, the residue was redissolved in 20 mL of DCM and washed with a 2% solution of sodium carbonate in water. The organic layer was dried over MgSO$_4$ and evaporated, yielding 0.05 g (62%) of intermediate M-2 N-[(2R,3S)-3-amino-2-hydroxy-4-phenylbutyl]-N-(2-methylpropyl)-[4-(2-methyloxazol-4-yl)phenyl]sulfonamide. Mass spectral data: m/z=458 (M+H)

Example 12

Synthesis of Imidazoles

Preparation of the Compounds of Formula (L-1)

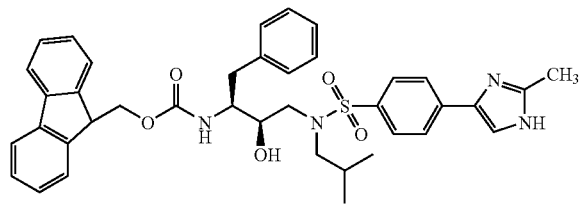

To 0.100 g intermediate K-1 in 5 mL of DMF was added 0.015 g of potassium acetate. The mixture was heated at 60° C. during 2 days then evaporated, yielding 98 mg (94%) of the desired intermediate [(1S,2R)-3-[N-[4-(acetyloxyacetyl)phenylsulfonyl]-N-(2-methylpropyl)amino]-2-hydroxy-1-(phenylmethyl)propyl]carbamic acid, 9-fluorenylmethylester. Mass spectral data: m/z=699 (M+H).

To 0.098 g of the previous intermediate in 5 mL acetic acid was added 0.043 g ammonium acetate. The mixture was heated overnight at 95° C., then evaporated and purified by preparative HPLC, yielding 0.015 g of intermediate L-3 [(1S,2R)-2-hydroxy-3-[N-[4-(2-methylimidazol-4-yl)phenylsulfonyl]-N-(2-methylpropyl)amino]-1-(phenylmethyl)propyl] carbamic acid, 9-fluorenylmethylester. Mass spectral data: m/z=679 (M+H).

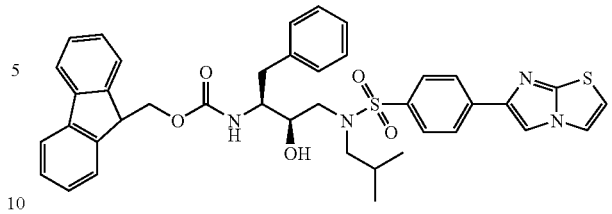

To 0.215 g of intermediate K-1 in 20 mL ethanol was added 0.040 g 2-aminothiazole. The mixture was heated at 90° C. overnight then evaporated, yielding 216 mg (100%) of the desired intermediate [(1S,2R)-3-[N-[4-(imidazo[2,1-b]thiazol-6-yl)phenylsulfonyl]-N-(2-methylpropyl)amino]-2-hydroxy-1-(phenylmethyl)propyl]carbamic acid, 9-fluorenylmethylester. Mass spectral data: m/z=721 (M+H).

Example 13

Preparation of the Compounds of Formula (L-3)

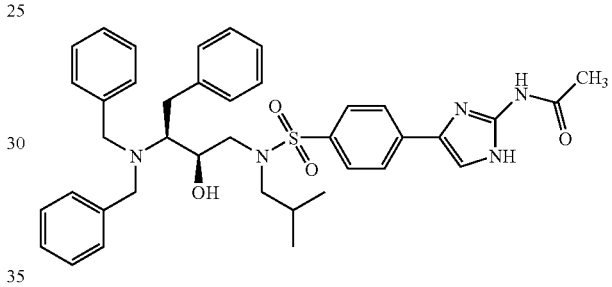

To 0.5 g of intermediate K-3 in 50 mL THF was added 0.075 g acetylguanidine. After overnight heating at reflux, 0.15 g acetylguanidine were added and the reflux was continued during 3 h. The solvent was evaporated and the residue dissolved in DCM, washed with water, dried over MgSO$_4$ and evaporated. The crude compound was purified on silica gel eluting with 20% ethyl acetate in dichloromethane, yielding 0.2 g (45%) of intermediate L-3 N-[(2R,3S)-3-(N',N'-dibenzyl)amino-2-hydroxy-4-phenylbutyl]-N-(2-methylpropyl)-4-[2-(acetylamino)imidazol-4-yl]phenylsulfonamide. Mass spectral data: m/z=680 (M+H).

Example 14

Preparation of the Compounds of Formula (M-3)

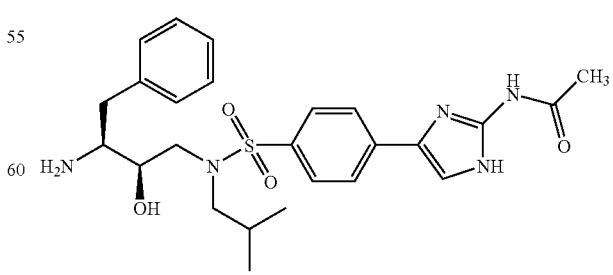

To a mixture of 0.2 g of intermediate L-3 in MeOH and potassium acetate was added 0.1 g of Pd/C 10%. The mixture was stirred with H₂ overnight, then 0.1 g of Pd/C 10% was again added. After stirring overnight with H₂, the mixture was filtered over celite and evaporated. The residue was redissolved in DCM, washed with water, dried over MgSO₄ and evaporated to yield 0.05 g (33%) of intermediate M-3 N-[(2R, 3S)-3-amino-2-hydroxy-4-phenylbutyl]-N-(2-methylpropyl)-[4-(2-acetylaminoimidazol-4-yl)-phenyl]sulfonamide. Mass spectral data: m/z=500 (M+H).

Example 15

Preparation of the Compounds of Formula (E)

Preparation of Compound 1 and Compound 36

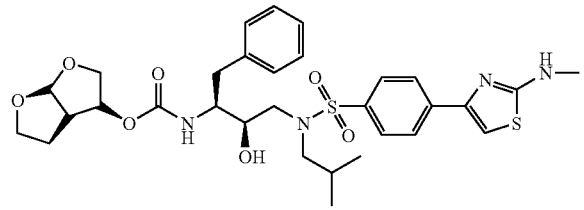

To a mixture of 0.21 g of intermediate M-1 in 25 mL of DCM was added 0.248 g of 1-[[(3R,3aS,6aR)-hexahydrofuro[2,3-b]furan-3-yl]oxycarbonyloxy]-2,5-pyrrolidinedione (prepared analogously to the procedure described in WO9967417) and 0.048 g of triethylamine. The reaction mixture was stirred at room temperature overnight and evaporated. The crude compound was purified on silica gel eluting with 2% methanol in dichloromethane, yielding 0.19 g (68%) of the desired final compound [(1S,2R)-2-hydroxy-3-[N-[4-(2-methylaminothiazol-4-yl)phenylsulfonyl]-N-(2-methylpropyl)amino]-1-(phenylmethyl)propyl]carbamic acid, [(3R, 3aS,6aR)-hexahydrofuro[2,3-b]furan-3-yl]ester. Mass spectral data: m/z=645 (M+H).

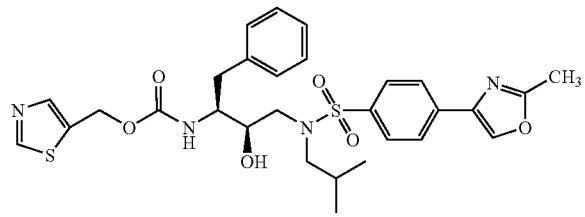

To a mixture of 0.015 g of 5-hydroxymethylthiazole in 5 mL of DCM were added 0.034 g of disuccinimidylcarbonate and 0.018 mL of triethylamine. The mixture was stirred at room temperature during 2 hours, then 0.050 g of intermediate M-2 was added and the mixture stirred overnight. The mixture was diluted with 5 mL of DCM, washed with a 2% solution of sodium carbonate in water, then brine, dried over MgSO₄ and evaporated. The crude compound was purified on silica gel eluting with 5% methanol in dichloromethane, yielding 0.026 g (36%) of the desired final compound [(1S, 2R)-2-hydroxy-3-[N-[4-(2-methyloxazol-4-yl)phenylsulfonyl]-N-(2-methylpropyl)amino]-1-(phenylmethyl)propyl]carbamic acid, (thiazol-5-ylmethyl)ester. Mass spectral data: m/z=599 (M+H).

Example 16

Synthesis of Compound 38

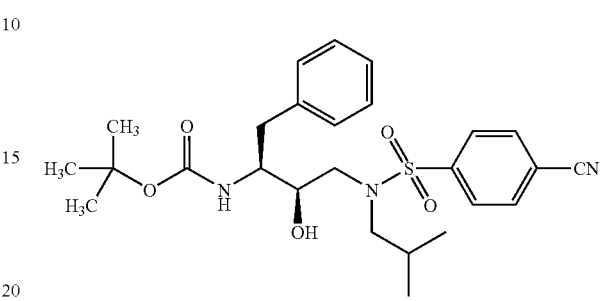

To a mixture of 13.44 g of intermediate A (PG:Boc) in 400 mL of DCM was added 8.08 g of triethylamine. The mixture was then cooled down to 0° C. and 8.87 g of 4-cyanobenzene sulfonylchloride dissolved in 100 mL of DCM were added dropwise. The mixture was then allowed to warm up to room temperature, stirred overnight and washed with water. The organic layer was dried over MgSO₄ and concentrated to yield 19.4 g (96%) of the desired sulfonamide [(1S,2R)-3-[N-(4-cyanophenylsulfonyl)-N-(2-methylpropyl)amino]-2-hydroxy-1-(phenyl methyl)propyl]carbamic acid, 1,1-dimethylethyl ester.

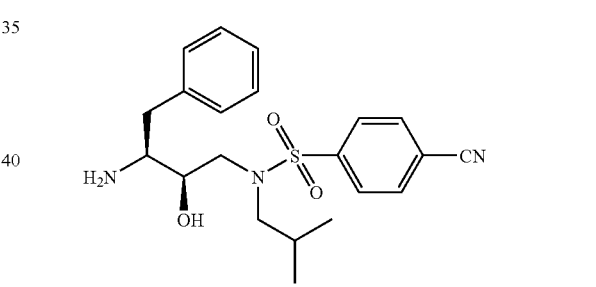

To a mixture of 9 g of the previous intermediate in 100 mL of DCM was added dropwise 20.5 g of trifluoroacetic acid, at 0° C. The mixture was stirred overnight at room temperature, washed with a saturated solution of sodium carbonate, then brine, dried over MgSO₄ and concentrated to yield 6.4 g (88%) of the desired amine N-[(2R,3S)-3-amino-2-hydroxy-4-phenylbutyl]-N-(2-methylpropyl)-4-cyanophenylsulfonamide (K-5).

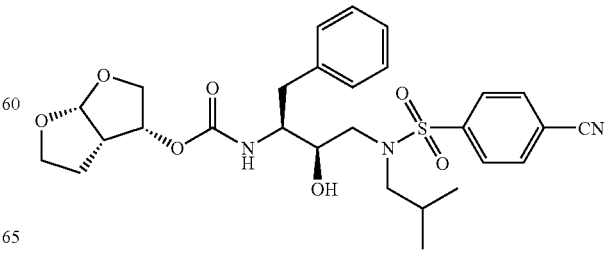

To a mixture of 6.4 g of the previous intermediate in 100 mL of DCM was added 4.75 g of 1-[[[[(3R,3aS,6aR)-hexahydrofuro[2,3-b]furan-3-yl]oxy]carbonyl]oxy]-2,5-pyrrolidinedione (prepared analogously to the procedure described in WO9967417) and 1.77 g of triethylamine. The reaction mixture was stirred at room temperature overnight and evaporated. The crude compound was purified on silica gel eluting with 30% ethyl acetate in dichloromethane, yielding 4.86 g (55%) of the desired compound [(1S,2R)-3-[N-(4-cyanophenylsulfonyl)-N-(2-methylpropyl)amino]-2-hydroxy-1-(phenylmethyl)-propyl]carbamic acid, [(3R,3aS,6aR)-hexahydrofuro[2,3-b]furan-3-yl]ester.

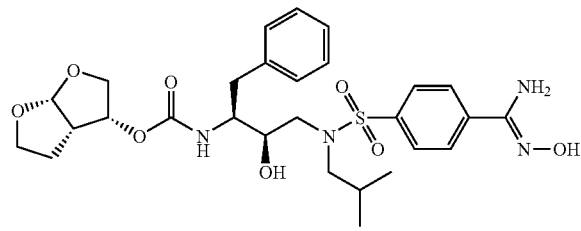

To a mixture of 4.8 g of the previous intermediate in 100 mL of ethanol were added 7.12 g of potassium carbonate and 2.98 g of hydroxylamine chlorhydrate. The mixture was refluxed overnight and concentrated. The residue was dissolved in ethyl acetate and washed with water, dried over MgSO₄ and concentrated to yield 4.88 g (96%) of the desired compound [(1S,2R)-2-hydroxy-3-[N-[4-[(hydroxyimino)aminomethyl]-phenylsulfonyl]-N-(2-methylpropyl)amino]-1-(phenylmethyl)propyl]carbamic acid, [(3R,3aS,6aR)-hexahydrofuro[2,3-b]furan-3-yl]ester.

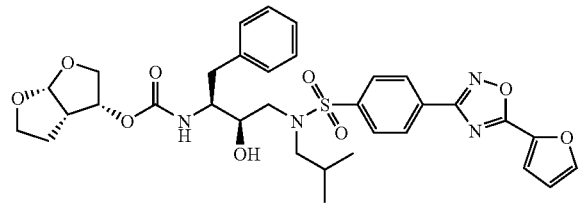

To a mixture of 0.5 g of the previous intermediate in 10 mL of pyridine was added 0.11 g of 2-furanoyl chloride. The mixture was refluxed during 4 hours and concentrated. The residue was dissolved in ethyl acetate, washed with water, dried over MgSO₄ and concentrated to yield 0.28 g (49%) of the desired oxadiazole derivative [(1S,2R)-3-[N-[4-(5-(furan-2-yl)oxadiazol-3-yl)phenylsulfonyl]-N-(2-methylpropyl)amino]-2-hydroxy-1-(phenylmethyl)propyl]carbamic acid, [(3R,3aS,6aR)-hexahydrofuro[2,3-b]furan-3-yl]ester. Mass spectral data: m/z=667 (M+H).

Example 17

Synthesis of Compound 56

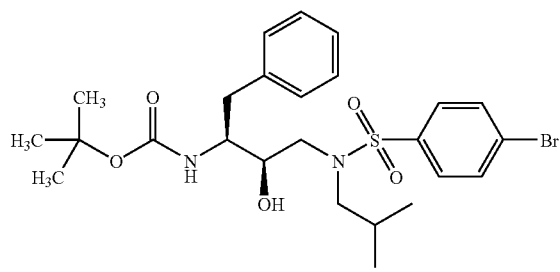

To a mixture of 12 g of intermediate A (PG:Boc) in 300 mL of DCM were added 6 mL of triethylamine and 9.6 g of 4-bromobenzene sulfonyl chloride, at 0° C. The mixture was stirred during 3 hours, washed with water, dried over MgSO₄ and concentrated to yield 20 g (100%) of the desired intermediate [(1S,2R)-3-[N-(4-bromophenylsulfonyl)-N-(2-methylpropyl)amino]-2-hydroxy-1-(phenylmethyl)propyl]carbamic acid, 1,1-dimethylethyl ester. Mass spectral data: m/z=556 (M+H).

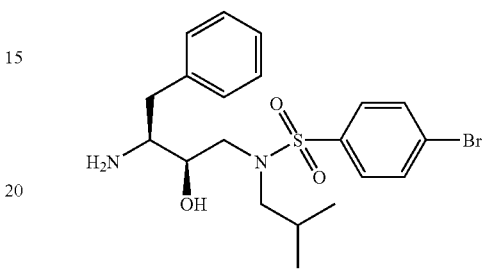

To a mixture of 10 g of the previous intermediate in 150 mL of DCM was added 13.9 mL of trifluoroacetic acid at 0° C. The mixture was stirred overnight and concentrated. The residue was treated with a mixture of DCM and a saturated solution of sodium carbonate in water. The organic layer was separated, dried over MgSO₄ and concentrated to yield 6.8 g (85%) of the deprotected compound N-[(2R,3S)-3-amino-2-hydroxy-4-phenylbutyl]-N-(2-methylpropyl)-4-bromophenylsulfonamide. Mass spectral data: m/z=456 (M+H).

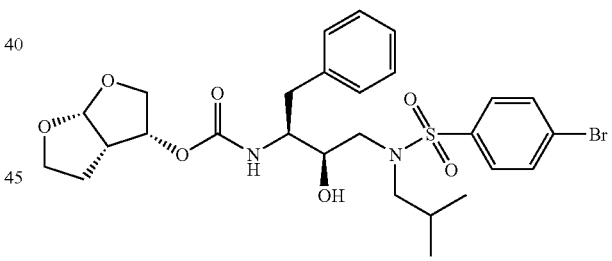

To a mixture of 6.8 g of the previous intermediate in 300 mL of DCM was added 4 g of 1-[[[[(3R,3aS,6aR)-hexahydrofuro[2,3-b]furan-3-yl]oxy]carbonyl]oxy]-2,5-pyrrolidine-dione (prepared analogously to the procedure described in WO9967417) and 2.7 mL of triethylamine. The reaction mixture was stirred at room temperature overnight, washed with a saturated solution of sodium bicarbonate in water, dried over MgSO₄ and evaporated. The crude compound was purified on silica gel eluting with 2% methanol in dichloromethane, yielding 6 g (65%) of the desired compound [(1S,2R)-3-[N-(4-bromophenylsulfonyl)-N-(2-methylpropyl)amino]-2-hydroxy-1-(phenylmethyl)propyl]-carbamic acid, [(3R,3aS,6aR)hexahydrofuro[2,3-b]furan-3-yl]ester. Mass spectral data: m/z=612 (M+H).

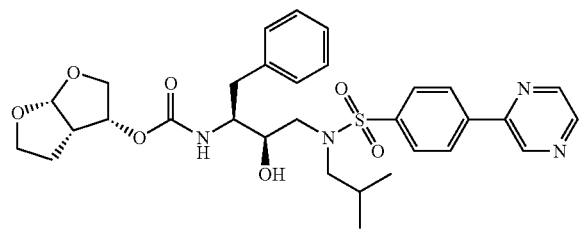

To a mixture of 61 mg of the previous intermediate in 5 mL of dioxane were added 41 mg of 2-pyrazinyltributyltin, 10 mg of triethylamine and 7 mg of PdCl$_2$(dppf)CH$_2$Cl$_2$ dichloro[1,1'-bis(diphenylphosphino)ferrocene]palladium(II) dichloromethane adduct. The reaction mixture was stirred overnight at 85° C. and evaporated. The crude mixture was purified by preparative HPLC to yield 4 mg of the desired compound [(1S,2R)-2-hydroxy-3-[N-(2-methylpropyl)-N-[4-(pyrazin-2-yl)-phenylsulfonyl]amino]-1-(phenylmethyl)propyl]carbamic acid, [(3R,3aS,6aR)-hexahydrofuro[2,3-b]furan-3-yl] ester. Mass spectral data: m/z=611 (M+H).

The compounds in the following tables were prepared according to one of the above disclosed methods. In the tables below (Table 1-6) the column "synthesis", indicates the general pathway through which a compound may be prepared.

TABLE 1

| N° | Ra | Rb | Synthesis | pEC$_{50}$ | Stereochemistry(Ra) |
|---|---|---|---|---|---|
| 1 | hexahydrofuro[2,3-b]furan-3-yl | —NH—CH$_3$ | 3.1 | 8.5 | (3R, 3aS, 6aR) |
| 2 | hexahydrofuro[2,3-b]furan-3-yl | —NH$_2$ | 3.1 | 8.5 | (3R, 3aS, 6R) |
| 3 | hexahydrofuro[2,3-b]furan-3-yl | —NH—C(O)—CH$_3$ | 3.1 | 8.3 | (3R, 3aS, 6aR) |
| 4 | hexahydrofuro[2,3-b]furan-3-yl | —NH—CH$_2$—CH$_2$—pyrrolidinyl | 3.1 | 7.9 | (3R, 3aS, 6aR) |
| 5 | hexahydrofuro[2,3-b]furan-3-yl | —NH—(4-pyridyl) | 3.1 | 7.6 | (3R, 3aS, 6aR) |
| 6 | hexahydrofuro[2,3-b]furan-3-yl | —NH—CH$_2$—CH$_2$—N(CH$_3$)$_2$ | 3.1 | 7.5 | (3R, 3aS, 6aR) |
| 7 | hexahydrofuro[2,3-b]furan-3-yl | —NH$_2$(Rb) and —CH$_3$ at position 5 on thiazolyl moiety | 3.1 | 7.3 | (3R, 3aS, 6aR) |

TABLE 1-continued
| N° | Ra | Rb | Synthesis | pEC$_{50}$ | Stereochemistry(Ra) |
|---|---|---|---|---|---|
| 8 | 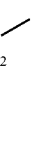 | —NH$_2$ | 3.1 | 5.9 | — |
| 9 | 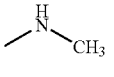 |  | 3.1 | 5.9 | — |
| 10 | 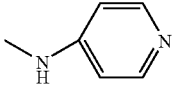 |  | 3.1 | 5.5 | — |
| 11 | 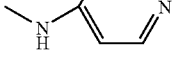 |  | 3.1 | 5.4 | — |
| 12 |  |  | 3.1 | 5.3 | — |
| 13 |  | —NH$_2$ | 3.1 | 5.3 | — |
| 14 | 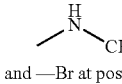 |  and —Br at position 5 on thiazolyl moiety | 3.1 | 5.3 | — |

TABLE 1-continued
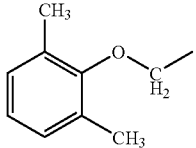
| N° | Ra | Rb | Synthesis | pEC$_{50}$ | Stereochemistry(Ra) |
|---|---|---|---|---|---|
| 15 | 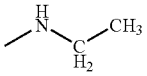 | 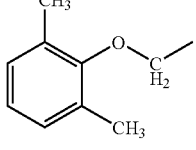 | 3.1 | 5.3 | — |
| 16 | 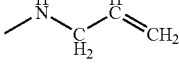 | 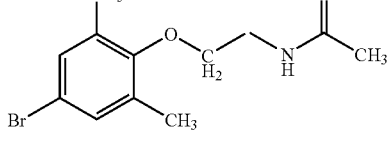 | 3.1 | 5.1 | — |
| 17 |  | 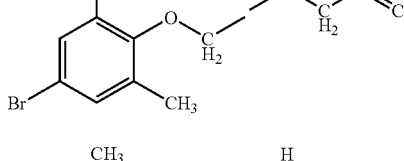 | 3.1 | 4.2 | — |
| 18 |  | 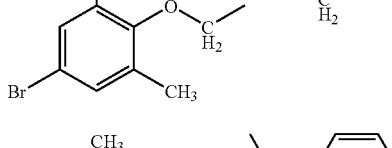 | 3.1 | 4.4 | — |
| 19 |  | 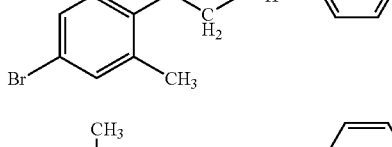 | 3.1 | 4.6 | — |
| 20 |  | 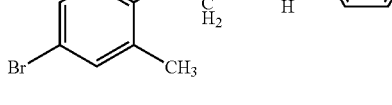 | 3.1 | 4.0 | — |
| 21 |  | | 3.1 | 4.7 | — |

TABLE 1-continued
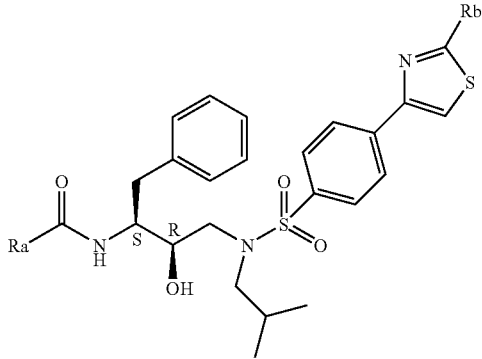
| N° | Ra | Rb | Synthesis | pEC₅₀ | Stereochemistry(Ra) |
|----|----|----|-----------|-------|---------------------|
| 22 | 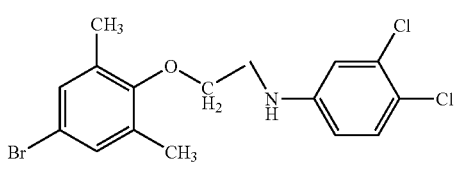 | 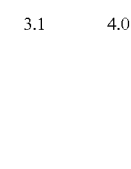 | 3.1 | 4.0 | — |
| 23 | 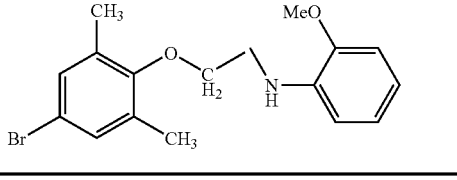 |  | 3.1 | 4.0 | — |
TABLE 2
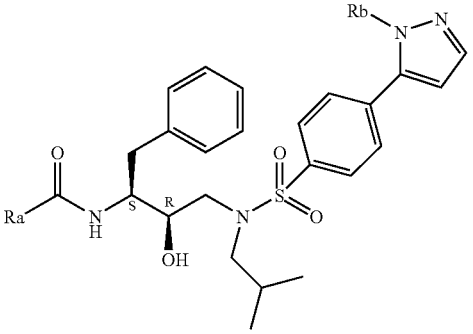
| N° | Ra | Rb | Synthesis | pEC₅₀ | Stereochemistry(Ra) |
|----|----|----|-----------|-------|---------------------|
| 24 | 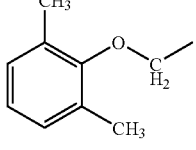 | —H | 3.4 | 7.1 | — |
| 25 | 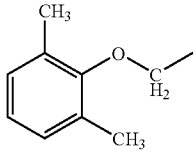 | —CH₃ | 3.4 | 5.9 | — |

TABLE 2-continued
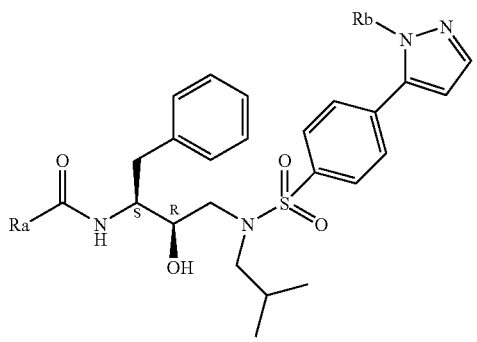
| N° | Ra | Rb | Synthesis | pEC$_{50}$ | Stereochemistry(Ra) |
|---|---|---|---|---|---|
| 26 | 2,6-dimethylphenoxy-CH$_2$- | -CH$_2$-CH(CH$_3$)-C(O)-O-CH$_2$-CH$_3$ | 3.4 | 5.7 | — |
| 27 | 2,6-dimethylphenoxy-CH$_2$- | -CH$_2$-C(CH$_3$)$_3$ | 3.4 | 5.2 | — |
| 28 | 2,6-dimethylphenoxy-CH$_2$- | -CH$_2$-CH$_2$-phenyl | 3.4 | 5.2 | — |
| 29 | 2,6-dimethylphenoxy-CH$_2$- | —CH$_2$—CH$_3$ | 3.4 | 5.2 | — |
| 30 | 2,6-dimethylphenoxy-CH$_2$- | —CH$_2$—CH$_2$—CH$_3$ | 3.4 | 5.0 | — |

TABLE 3

| N° | Ra | Rb | Synthesis | pEC$_{50}$ | Stereochemistry(Ra) |
|---|---|---|---|---|---|
| 31 | hexahydrofuro[2,3-b]furan-3-yl-OMe (6a,3a,3) | —CH$_3$ | 3.3 | 7.6 | (3R, 3aS, 6aR) |
| 32 | hexahydrofuro[2,3-b]furan-3-yl-OMe | —NH-C(O)-CH$_3$ | 3.3 | 7.7 | (3R, 3aS, 6aR) |
| 33 | hexahydrofuro[2,3-b]furan-3-yl-OMe | hexahydrofuro[2,3-b]furan-3-yl-O-C(O)-NH— | 3.3 | 6.7 | (3R, 3aS, 6aR) |
| 34 | hexahydrofuro[2,3-b]furan-3-yl-OMe | —NH$_2$ | 3.3 | 6.2 | (3R, 3aS, 6ar) |

TABLE 4

| N° | Ra | Rb | Synthesis | pEC$_{50}$ | Stereochemistry (Ra) |
|---|---|---|---|---|---|
| 35 | hexahydrofuro[2,3-b]furan-3-yl-OMe (6a,3a,3) | —CH$_3$ | 3.2 | 8.4 | (3R, 3aS, 6aR) |
| 36 | thiazol-5-yl-CH$_2$-OMe | —CH$_3$ | 3.2 | 6.3 | — |

TABLE 4-continued

| N° | Ra | Rb | Synthesis | pEC₅₀ | Stereochemistry (Ra) |
|---|---|---|---|---|---|
| 37 | (hexahydrofuro[2,3-b]furan-3-yl, 3a,6a positions) with OMe at 3 | —NH₂ | 3.2 | 8.4 | (3R, 3aS, 6aR) |

TABLE 5

| N° | Ra | Rb | Synthesis | pEC₅₀ | Stereochemistry(Ra) |
|---|---|---|---|---|---|
| 38 | hexahydrofuro-furan-OMe | 2-furyl | 4 | 8.4 | (3R, 3aS, 6aR) |
| 39 | hexahydrofuro-furan-OMe | —CH₂—O—CH₂—phenyl | 4 | 8.1 | (3R, 3aS, 6aR) |
| 40 | hexahydrofuro-furan-OMe | —CH₂—CH₂—CH₃ | 4 | 8.5 | (3R, 3aS, 6aR) |
| 41 | hexahydrofuro-furan-OMe | —CH₂—CH₂—C(=O)—O— | 4 | 7.2 | (3R, 3aS, 6aR) |

TABLE 5-continued

| N° | Ra | Rb | Synthesis | pEC$_{50}$ | Stereochemistry(Ra) |
|---|---|---|---|---|---|
| 42 | hexahydrofuro[2,3-b]furan-3-yloxy (3a,6a,3) | -CH$_2$CH$_2$CH$_2$-C(O)-O-CH$_2$CH$_3$ | 4 | 7.7 | (3R, 3aS, 6aR) |
| 43 | hexahydrofuro[2,3-b]furan-3-yloxy | 4-NO$_2$-phenyl | 4 | 7.9 | (3R, 3aS, 6aR) |
| 44 | hexahydrofuro[2,3-b]furan-3-yloxy | 3-OMe-phenyl | 4 | 8.0 | (3R, 3aS, 6aR) |
| 45 | hexahydrofuro[2,3-b]furan-3-yloxy | benzo[1,3]dioxol-5-yl | 4 | 7.8 | (3R, 3aS, 6aR) |
| 46 | hexahydrofuro[2,3-b]furan-3-yloxy | 3,5-dimethylisoxazol-4-yl | 4 | 8.4 | (3R, 3aS, 6aR) |
| 47 | hexahydrofuro[2,3-b]furan-3-yloxy | 4-I-phenyl | 4 | 7.1 | (3R, 3aS, 6aR) |
| 48 | hexahydrofuro[2,3-b]furan-3-yloxy | 1-phenyl-ethyl acetate | 4 | 8.3 | (3R, 3aS, 6aR) |
| 49 | hexahydrofuro[2,3-b]furan-3-yloxy | -CH$_2$-CH(CH$_3$)$_2$ | 4 | 8.1 | (3R, 3aS, 6aR) |
| 50 | hexahydrofuro[2,3-b]furan-3-yloxy | thiophen-2-yl | 4 | 8.0 | (3R, 3aS, 6aR) |

TABLE 5-continued
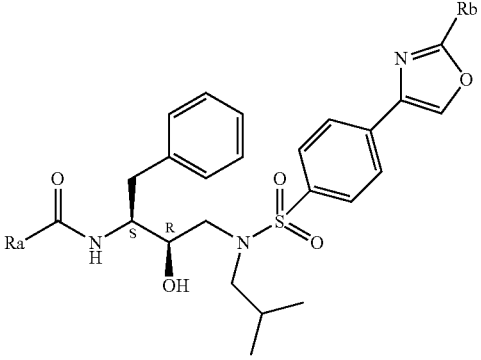
| N° | Ra | Rb | Synthesis | pEC₅₀ | Stereochemistry(Ra) |
|---|---|---|---|---|---|
| 51 | (furofuran-OMe) | 4-Br-phenyl | 4 | 7.5 | (3R, 3aS, 6aR) |
| 52 | (furofuran-OMe) | 4-CN-phenyl | 4 | 8.1 | (3R, 3aS, 6aR) |
TABLE 6
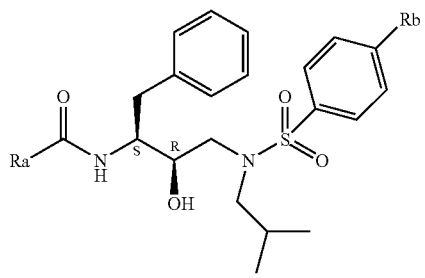
| N° | Ra | Rb | Synthesis | pEC₅₀ | Stereochemistry(Ra) |
|---|---|---|---|---|---|
| 53 | (furofuran-OMe) | imidazo[2,1-b]thiazole | 5 | 7.6 | (3R, 3aS, 6aR) |
| 54 | (furofuran-OMe) | tetrazole | 5 | — | (3R, 3aS, 6aR) |
| 55 | (furofuran-OMe) | benzo[1,3]dioxole | 5 | — | (3R, 3aS, 6aR) |
| 56 | (furofuran-OMe) | pyrazine | 5 | 8.1 | (3R, 3aS, 6aR) |
| 57 | (furofuran-OMe) | pyridine | 5 | 7.7 | (3R, 3aS, 6aR) |

TABLE 6-continued

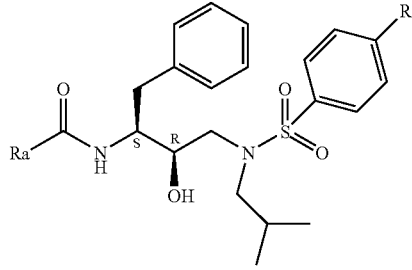

| N° | Ra | Rb | Synthesis | pEC$_{50}$ | Stereochemistry(Ra) |
|----|----|----|-----------|-----------|---------------------|
| 58 | 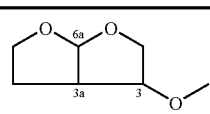 | 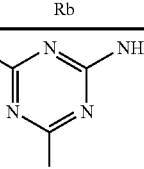 | 5 | 6.0 | (3R, 3aS, 6aR) |

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method:

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as EC$_{50}$ and EC$_{90}$. These values represent the amount of the compound required to protect 50% and 90%, respectively, of the cells from the cytopathogenic effect of the virus. The toxicity of the compound was measured on the mock-infected cells and was expressed as CC$_{50}$, which represents the concentration of compound required to inhibit the growth of the cells by 50%. The selectivity index (SI) (ratio CC$_{50}$/EC$_{50}$) is an indication of the selectivity of the anti-HIV activity of the inhibitor. Wherever results are reported as e.g. pEC$_{50}$ or pCC$_{50}$ values, the result is expressed as the negative logarithm of the result expressed as EC$_{50}$ or CC$_{50}$ respectively.

Antiviral Spectrum:

Because of the increasing emergence of drug resistant HIV strains, the present compounds were tested for their potency against clinically isolated HIV strains harboring several mutations (Table 7 and 8). These mutations are associated with resistance to protease inhibitors and result in viruses that show various degrees of phenotypic cross-resistance to the currently commercially available drugs such as for instance saquinavir, ritonavir, nelfinavir, indinavir and amprenavir.

TABLE 7

List of mutations present in the protease gene of the HIV strains (A to F) used.

| | |
|---|---|
| A | V003I, L010I, V032T, L033M, E035D, S037Y, S037D, M046I, R057R/K, Q058E, L063P, K070T, A071V, I072V, I084V, L089V |
| B | V003I, L010I, K020R, E035D, M036I, S037N, Q058E, I062V, L063P, A071V, I072M, G073S, V077I, I084V, I085V, L090M |
| C | V003I, L010I, I015V, L019I, K020M, S037N, R041K, I054V, Q058E, L063P, A071V, I084V, L090M, I093L |
| D | V003I, L010L/I, I013V, L033I, E035D, M036I, M046L, K055R, R057K, L063P, I066F, A071V, I084V, N088D, L090M |
| E | V003I, L010I, V011I, A022V, L024I, E035D, M036I, S037T, R04IK, I054V, I062V, L063P, A071V, I084V |
| F | L010F, M046I, M071V, I084V |

Results:

As a measure of the broad spectrum activity of the present compounds, the fold resistance (FR), defined as FR=EC$_{50}$ (mutant strain)/EC$_{50}$ (HIV-1 strain LAI), was determined. Table 8 shows the results of the antiviral testing in terms of fold resistance. As can be seen in this table, the present compounds are effective in inhibiting a broad range of mutant strains: Column A: FR value towards mutant A; Column B: FR towards mutant B; Column C: FR towards mutant C; Column D: FR towards mutant D; Column E: FR towards mutant E; Column F: FR towards mutant F. The toxicity (Tox) is expressed as the pCC$_{50}$ value as determined with mock transfected cells. Column WT displays the pEC$_{50}$ value against wild type HIV-LAI strain.

TABLE 8

Results of the toxicity testing and the resistance testing against strain A to F (expressed as FR). NA indicates not available

| N° | A | B | C | D | E | F | Tox | WT |
|----|------|------|------|------|------|------|-------|-----|
| 1  | 5.4  | 2.1  | 1.2  | 7.9  | 5.0  | 42   | 4.19  | 8.5 |
| 2  | 26   | 10.0 | 3.0  | 9.3  | 8.9  | 91   | 4.07  | 8.5 |
| 3  | 39   | 8.9  | 7.4  | 26   | 17   | 151  | 4.11  | 8.3 |
| 5  | 22.3 | 6.3  | 3.0  | NA   | 13.5 | NA   | 4.95  | 7.6 |
| 6  | 6.2  | 4.7  | 1.2  | 3.8  | 6.6  | 79   | 4.69  | 7.5 |
| 24 | 1.1  | NA   | NA   | NA   | 3.1  | NA   | 4.2   | 7.1 |
| 32 | 1.3  | 1.0  | 0.33 | NA   | 0.95 | 7.2  | <4.0  | 7.7 |

TABLE 8-continued

Results of the toxicity testing and the resistance testing against strain A to F (expressed as FR). NA indicates not available

| N° | A | B | C | D | E | F | Tox | WT |
|---|---|---|---|---|---|---|---|---|
| 33 | 0.71 | 0.66 | 0.2 | NA | 0.19 | 2.6 | <4.0 | 6.7 |
| 35 | 11 | 10.5 | 8.3 | 6.2 | 8.3 | 42 | <4.0 | 8.4 |
| 38 | 30 | 23 | 6.8 | 14.8 | 9.5 | 44.7 | <4.49 | 8.4 |
| 39 | 36 | NA | NA | NA | 52 | NA | <4.0 | 8.1 |
| 40 | 5.0 | NA | 4.1 | 12.9 | 41 | 219 | <4.49 | 8.5 |
| 42 | 6.2 | 7.8 | 1.7 | 6.2 | 6.2 | 30 | <4.0 | 7.7 |
| 43 | 54 | 23 | 9.1 | 10.2 | 6.6 | NA | <4.0 | 7.9 |
| 44 | 39 | 14 | 8.1 | 15 | 13 | 77 | <4.49 | 8.0 |
| 46 | 182 | 32 | 9.1 | 32 | 9.8 | NA | <4.49 | 8.4 |
| 48 | 89 | 25 | 5.8 | 17 | 6.9 | NA | <4.0 | 8.3 |
| 49 | NA | 21 | 4.4 | NA | 10 | NA | <4.49 | 8.1 |
| 50 | NA | 14 | 4.3 | 13 | NA | NA | <4.49 | 8.0 |
| 51 | NA | NA | 4.8 | 12 | 4.8 | NA | <4.49 | 7.5 |
| 52 | NA | 17 | 6.2 | 16 | 11 | NA | <4.49 | 8.1 |
| 57 | 49 | 23 | 5.6 | 27 | 8.3 | NA | 4.83 | 7.7 |

Bioavailability:

The bioavailability of the present compounds was measured in rats. The compounds were administered orally or intraperitoneally. Animals were sacrificed at different time points after administration, whole blood was collected and serum prepared by standard methods. Concentration of the compound in serum was determined by titrating the anti-HIV activity present in the sample according to the procedure described above. Serum concentrations were also measured by HPLC-MS.

Protein Binding Analyses:

Human serum proteins like albumin (HSA) or alpha-1 acid glycoprotein (AAG) are known to bind many drugs, resulting in a possible decrease in the effectiveness of those compounds. In order to determine whether the present compounds would be adversely effected by this binding, the anti-HIV activity of the compounds was measured in the presence of human serum, thus evaluating the effect of the binding of the protease inhibitors to those proteins.

Formulation

Active ingredient, in casu a compound of formula (I), was dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, were dissolved in organic solvents such as ethanol, methanol methylene chloride. Suitably the polymer was dissolved in ethanol. The polymer and compound solutions were mixed and subsequently spray dried. The ratio of compound/polymer was selected from 1/1 to 1/6. Intermediate ranges were 1/1.5 and 1/3. A suitable ratio was 1/6. The spraydried powder, a solid dispersion, is subsequently filled in capsules for administration. The drug load in one capsule ranges between 50 and 100 mg depending on the capule size used.

Film-Coated Tablets

Preparation of Tablet Core

A mixture of 100 g of active ingredient, in casu a compound of formula (I), 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methylcellulose in 75 ml of denaturated ethanol there was added a solution of 5 g of ethylcellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

The invention claimed is:

1. A compound having the formula

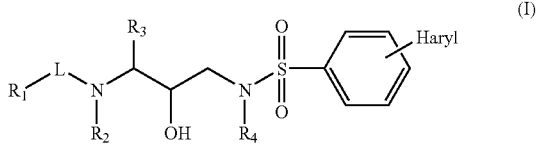

(I)

an N-oxide, salt, stereoisomeric form, or racemic mixture, thereof, wherein $R_1$—L— is $Het^1$-O—C(=O)— whereby the C(=O) group is attached to the $NR_2$ moiety;

$R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl $C_{1-6}$alkyl, aryl, $Het^1$, $Het^1C_{1-6}$alkyl, $Het^2$, $Het^2 C_{1-6}$alkyl;

$R_1$ may also be a radical of formula

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; whereby $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, $Het^1$oxycarbonyl, $Het^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, $Het^1$ carbonyl, Het¹carbonyloxy, Het¹C$_{1-4}$alkyloxycarbonyl, Het²-carbonyloxy, Het²C$_{1-4}$alkylcarbonyloxy, Het² C$_{1-4}$alkyloxycarbonyloxy or C$_{1-4}$alkyl optionally substituted with aryl, aryloxy, Het² or hydroxy; wherein the substituents on the amino groups are each independently selected from C$_{1-4}$alkyl, aryl, arylC$_{1-4}$alkyl, C$_{3-7}$cycloalkyl, C$_{3-7}$cycloalkylC$_{1-4}$alkyl, Het¹, Het², Het¹C$_{1-4}$alkyl and Het²C$_{1-4}$alkyl;

$R_{11b}$ is hydrogen, C$_{3-7}$cycloalkyl, C$_{2-6}$alkenyl, C$_{2-6}$alkynyl, aryl, Het¹, Het² or C$_{1-4}$alkyl optionally substituted with halogen, hydroxy, C$_{1-4}$alkylS(=O)$_t$, aryl, C$_{3-7}$cycloalkyl, Het¹, Het², amino optionally mono- or disubstituted where the substituents are selected from C$_{1-4}$alkyl, aryl, arylC$_{1-4}$alkyl, C$_{3-7}$cycloalkyl, C$_{3-7}$cycloalkylC$_{1-4}$alkyl, Het¹, Het², Het¹C$_{1-4}$alkyl and Het²C$_{1-4}$alkyl;

whereby $R_{11b}$ may be linked to the remainder of the molecule via a sulfonyl group;

$R_2$ is hydrogen or C$_{1-6}$alkyl;

$R_3$ is C$_{1-6}$alkyl, aryl, C$_{3-7}$cycloalkyl, C$_{3-7}$cycloalkylC$_{1-4}$alkyl, or arylC$_{1-4}$alkyl;

$R_4$ is C$_{1-6}$alkyl, whereby C$_{1-6}$alkyl may optionally be substituted with a substituent selected from aryl, Het¹, Het², C$_{3-7}$cycloalkyl, C$_{1-4}$alkyloxycarbonyl, carboxyl, optionally mono- or disubstituted aminocarbonyl, optionally mono- or disubstituted aminosulfonyl, C$_{1-4}$alkylS(=O)$_t$, hydroxy, cyano, optionally mono- or disubstituted amino and halogen, and whereby the optional substituents on any amino function are independently selected from C$_{1-4}$alkyl, aryl, arylC$_{1-4}$alkyl, C$_{3-7}$cycloalkyl, C$_{3-7}$cycloalkylC$_{1-4}$alkyl, Het¹, Het², Het¹C$_{1-4}$alkyl and Het²C$_{1-4}$alkyl; t is zero, 1 or 2;

each t independently selected is zero, 1 or 2;

Haryl is an aromatic heterocycle having five ring members which contains one nitrogen, and one sulfur atom as ring members and which may optionally be substituted on (i) one or more carbon atoms by C$_{1-6}$alkyl, halogen, hydroxy, optionally mono- or disubstituted amino, nitro, cyano, haloC$_{1-6}$alkyl, carboxyl, C$_{3-7}$cycloalkyl, optionally mono- or disubstituted aminocarbonyl, methylthio, methylsulfonyl, aryl, —(R$_{7a}$)$_n$—M—R$_{7b}$, Het¹ and Het²; whereby the optional substituents on any amino function are independently selected from R$_5$ and —A—R$_6$; and on (ii) a nitrogen atom if present by hydroxy or —A—R$_6$;

A is C$_{1-6}$alkanediyl, —C(=O)—, —C(=S)—, —S(=O)$_2$—, C$_{1-6}$alkanediyl-C(=O)—, C$_{1-6}$alkanediyl-C(=S)— or C$_{1-6}$alkanediyl-S(=O)$_2$—; whereby for those groups containing a C$_{1-6}$alkanediyl moiety, the C$_{1-6}$alkanediyl moiety is attached to the amino group;

$R_5$ is hydroxy, C$_{1-6}$alkyl, Het¹C$_{1-6}$alkyl, Het²C$_{1-6}$alkyl, aminoC$_{1-6}$alkyl whereby the amino group may optionally be mono- or di-substituted with C$_{1-4}$alkyl;

$R_6$ is hydrogen, C$_{1-6}$alkyloxy, Het¹, Het¹oxy, Het², Het²oxy, aryl, aryloxy or amino; and in case —A— is other than C$_{1-6}$alkanediyl then R$^6$ may also be C$_{1-6}$alkyl, Het¹C$_{1-4}$alkyl, Het¹oxyC$_{1-4}$alkyl, Het²C$_{1-4}$alkyl, Het²oxyC$_{1-4}$alkyl, arylC$_{1-4}$alkyl, aryloxyC$_{1-4}$alkyl or aminoC$_{1-4}$alkyl; whereby each of the amino groups in the definition of R$_6$ may optionally be substituted with one or two substituents selected from C$_{1-4}$alkyl, C$_{1-4}$alkylcarbonyl, C$_{1-4}$alkyloxycarbonyl, aryl, arylcarbonyl, aryloxycarbonyl, Het¹, Het², arylC$_{1-4}$alkyl, Het¹C$_{1-4}$alkyl or Het²C$_{1-4}$alkyl;

$R_{7a}$ is C$_{1-8}$ alkanediyl optionally substituted with one or more substituents selected from, halogen, C$_{1-4}$alkylcarbonyl, C$_{1-4}$alkyloxycarbonyl, aryl, arylcarbonyl, aryloxycarbonyl, Het¹ or Het²;

$R_{7b}$ is C$_{1-8}$ alkyl optionally substituted with one or more substituents selected from halogen, C$_{1-4}$alkylcarbonyl, C$_{1-4}$alkyloxycarbonyl, aryl, arylcarbonyl, aryloxycarbonyl, Het¹ or Het²;

M is defined by —C(=O)—, —O—C(O)—, —C(O)—O—, —CH$_2$—CHOH—, —CHOH—CH$_2$—, —NR$_8$—C(O)—, —(C=O)—NR$_8$—, —S(=O)$_2$—, —O—, —S—, —O—S(=O)$_2$—, —S(=O)$_2$—O—, —NR$_8$—S(=O)$_2$ or —S(=O)$_2$—NR$_8$—;

n is zero or 1.

2. A compound selected from the group consisting of compounds numbers 1, 2, 3, 4, 5, and 6, said compounds having the following formula:

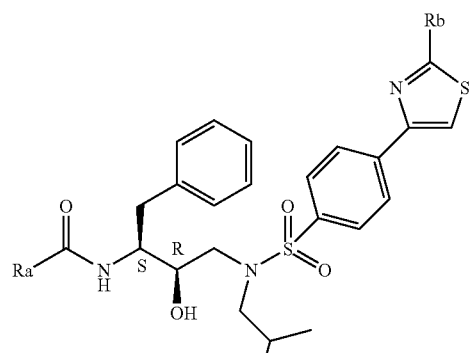

wherein Ra and Rb are the following:

| Compound Number | Ra | Rb | Stereochemistry (Ra) |
|---|---|---|---|
| 1 | (structure with 6a, 3a, 3 positions, O, O, O) | H-N-CH$_3$ | (3R, 3aS, 6aR) |

-continued

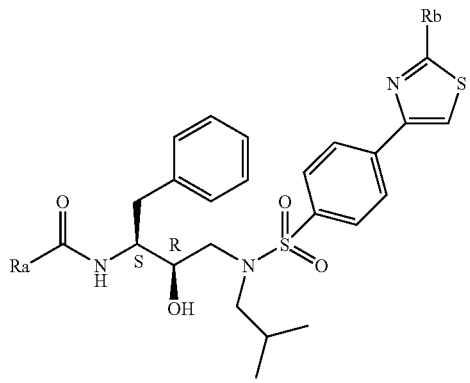

wherein Ra and Rb are the following:

| Compound Number | Ra | Rb | Stereochemistry (Ra) |
|---|---|---|---|
| 2 | (oxahexahydrofurofuranyl-O-) | —NH$_2$ | (3R, 3aS, 6aR) |
| 3 | (oxahexahydrofurofuranyl-O-) | —NHC(O)CH$_3$ | (3R, 3aS, 6aR) |
| 4 | (oxahexahydrofurofuranyl-O-) | —NHCH$_2$CH$_2$-pyrrolidinyl | (3R, 3aS, 6aR) |
| 5 | (oxahexahydrofurofuranyl-O-) | —NH-(4-pyridyl) | (3R, 3aS, 6aR) |
| 6 | (oxahexahydrofurofuranyl-O-) | —NHCH$_2$CH$_2$N(CH$_3$)$_2$ | (3R, 3aS, 6aR). |

3. A pharmaceutical composition, comprising an effective amount of at least one compound as claimed in claim 1, and a pharmaceutically tolerable excipient.

4. A pharmaceutical composition, comprising an effective amount of at least one compound as claimed in claim 1, and a modulator of the metabolization of said compound.

5. A compound as claimed in claim 1 for use as a medicine.

6. A method of inhibiting a protease of a retrovirus in a mammal infected with said retrovirus, comprising administering a protease inhibiting amount of a compound according to claim 1 to said mammal in need thereof.

7. A method of treating or combating infection or disease associated with retrovirus infection in a mammal, comprising administering an effective amount of at least one compound according to claim 1 to said mammal.

8. A method of treating or combating infection or disease associated with retrovirus infection in a mammal, comprising administering an effective amount of at least a first compound according to claim 1, further comprising administrating at least a second compound, modulating the metabolization of said first compound, to said mammal, wherein said second compound may be administered simultaneously, separately or sequentially with said first compound.

9. A method of inhibiting retroviral replication, comprising contacting a retrovirus with an effective amount of at least one compound according to claim 1.

10. A method according to claim 6, wherein the retrovirus is a human immunodeficiency virus (HIV).

11. A pharmaceutical composition consisting of a solid dispersion comprising, (a) a compound as claimed in any of claim 1, (b) one or more pharmaceutically acceptable water-soluble polymers.

12. A product containing at least one compound of formula (I) according to claim 1 and an antiretroviral agent as a combined preparation for the simultaneous, separate or sequential use in antiretroviral therapy.

13. A pharmaceutical composition, comprising an effective amount of at least one compound as claimed in claim 2, and a pharmaceutically tolerable excipient.

14. A pharmaceutical composition, comprising an effective amount of at least one compound as claimed in claim 2, and a modulator of the metabolization of said compound.

15. A compound as claimed in claim 2 for use as a medicine.

16. A method of inhibiting a protease of a retrovirus in a mammal infected with said retrovirus, comprising administering a protease inhibiting amount of a compound according to claim 2 to said mammal in need thereof.

17. A method of treating or combating infection or disease associated with retrovirus infection in a mammal, comprising administering an effective amount of at least one compound according to claim 2 to said mammal.

18. A method of treating or combating infection or disease associated with retrovirus infection in a mammal, comprising administering an effective amount of at least a first compound according to claim 2, further comprising administrating at least a second compound, modulating the metabolization of said first compound, to said mammal, wherein said second compound may be administered simultaneously, separately or sequentially with said first compound.

19. A method of inhibiting retroviral replication, comprising contacting a retrovirus with an effective amount of at least one compound according to claim 2.

20. A method according to claim 16, wherein the retrovirus is a human immunodeficiency virus (HIV).

21. A pharmaceutical composition consisting of a solid dispersion comprising, (a) a compound as claimed in any of claim 2, (b) one or more pharmaceutically acceptable water-soluble polymers.

22. A product containing at least one compound of formula (I) according to claim 2 and an antiretroviral agent as a combined preparation for the simultaneous, separate or sequential use in antiretroviral therapy.

* * * * *

UNITED STATES PATENT AND TRADEMARK OFFICE
CERTIFICATE OF CORRECTION

| | | |
|---|---|---|
| PATENT NO. | : 7,763,641 B2 | Page 1 of 1 |
| APPLICATION NO. | : 10/499221 | |
| DATED | : July 27, 2010 | |
| INVENTOR(S) | : Vendeville et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1629 days.

Signed and Sealed this
Fifteenth Day of March, 2011

David J. Kappos
*Director of the United States Patent and Trademark Office*